United States Patent [19]

Hall et al.

[11] Patent Number: 5,525,854
[45] Date of Patent: Jun. 11, 1996

[54] IN-PLANE ULTRASONIC VELOCITY MEASUREMENT

[75] Inventors: Maclin S. Hall, Marietta; Theodore G. Jackson, Atlanta; Christopher Knerr, Lawrenceville, all of Ga.

[73] Assignee: Institute of Paper Science and Technology, Inc., Atlanta, Ga.

[21] Appl. No.: 398,926

[22] Filed: Mar. 6, 1995

Related U.S. Application Data

[62] Division of Ser. No. 970,624, Nov. 3, 1992, Pat. No. 5,493,910.

[51] Int. Cl.$^6$ .................................................. H01L 41/08
[52] U.S. Cl. .............................. 310/334; 310/336; 73/644
[58] Field of Search .................................. 310/334–337; 73/642, 644, 632

[56] References Cited

U.S. PATENT DOCUMENTS

| | | | |
|---|---|---|---|
| Re. 29,785 | 9/1978 | Leschek et al. | 310/336 X |
| 3,541,840 | 11/1970 | Phelan | 310/334 X |
| 3,600,613 | 8/1971 | Clarke | 310/334 X |
| 3,628,375 | 12/1971 | Pagano | 310/334 X |
| 3,810,384 | 5/1974 | Evans | 73/67.85 |
| 4,174,636 | 11/1979 | Pagano | 73/597 |
| 4,291,577 | 9/1981 | Baum et al. | 73/597 |
| 4,574,634 | 3/1986 | Pappano | 310/334 |
| 4,713,572 | 12/1987 | Bokowski et al. | 310/323 |
| 4,730,492 | 3/1988 | Burk | 73/597 |
| 4,735,087 | 4/1988 | Hourani et al. | 73/597 |
| 4,750,368 | 6/1988 | Shearer et al. | 73/618 |
| 4,763,513 | 8/1988 | Zatharias | 73/644 |
| 4,769,571 | 9/1988 | Habeger, Jr. et al. | 310/334 |
| 4,841,223 | 6/1989 | Baum et al. | 324/53.5 A |
| 5,117,698 | 6/1992 | Baumoel | 73/861.28 |

OTHER PUBLICATIONS

"On–Machine Sensors To Measure Paper Mechanical Properties" by Dr. Maclin S. Hall, U.S. Department of energy, Advanced Sensor Technical Conference, Nov. 11, 1991.

"On–Machine Sensors To Measure Paper Mechanical Properties" by Dr. Maclin S. Hall and Charles C. Habeger, Jr. dated Oct. 1988.

"Using a Robot–Based Instrument to Measure the In–Plane Ultrasonic Velocities of Paper" by C. C. Habeger, M. L. Van Zummerman and W. A. Wink, *Tappi Journal*, pp. 171–175, Jul. 1989.

"On–Machine Sensors To Measure Paper Mechanical Properties" by Maclin S. Hall, Sensors Expo West Proceedings 1990, pp. 205A–1–205A–4.

"On–Line Ultrasonic Measurement of Paper Strength" by Maclin S. Hall, *Sensors*, Jun. 1990, pp. 13–20.

"Acousto–Ultrasonic Measurement Of Internal Bond Strength In Composite Wood Products" by John M. Rodgers, Allen T. Green and Stephen W. Borup, *Materials Evaluation*, May 1991, pp. 566–571.

(List continued on next page.)

*Primary Examiner*—Mark O. Budd
*Attorney, Agent, or Firm*—Fitch, Even, Tabin & Flannery

[57] ABSTRACT

An improved system for measuring the velocity of ultrasonic signals within the plane of moving web-like materials, such as paper, paperboard and the like. In addition to velocity measurements of ultrasonic signals in the plane of the web in the MD and CD, one embodiment of the system in accordance with the present invention is also adapted to provide on-line indication of the polar specific stiffness of the moving web. In another embodiment of the invention, the velocity of ultrasonic signals in the plane of the web are measured by way of a plurality of ultrasonic transducers carried by synchronously driven wheels or cylinders, thus eliminating undue transducer wear due to any speed differences between the transducers and the web. In order to provide relatively constant contact force between the transducers and the webs, the transducers are mounted in a sensor housings which include a spring for biasing the transducer radially outwardly. The sensor housings are adapted to be easily and conveniently mounted to the carrier to provide a relatively constant contact force between the transducers and the moving web.

7 Claims, 17 Drawing Sheets

OTHER PUBLICATIONS

"Ultrasonic Testing of Materials" by Josef Krautkramer and Herbert Krautkramer, Third Edition, 1983, p. 302.

"Thickness Direction Measurements In Paper Materials Using Ultrasonic Sensors Immersed In Water-Filled Wheels" by P. H. Brodeur, M. S. Hall, K. W. Lorenz and T. G. Jackson, Ultrasonics International 91 Conference Proceedings, Jul. 1991, pp. 331–334.

"On-Machine Sensors To Measure Paper Mechanical Properties" by M. Hall, P. Brodeur, K. Lorenz and T. Jackson, Presented at DOE/Industry Sensors Technical Conference in Nov. 1990.

"Sound Wave Dispersion And Attenuation In The Thickness Direction Of Paper" by P. Brodeur and M. S. Hall, Proceedings 1991 International Paper Physics Conference, Sep. 1991, pp. 109–114.

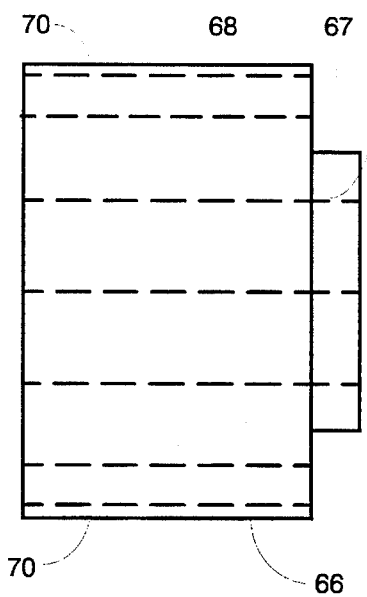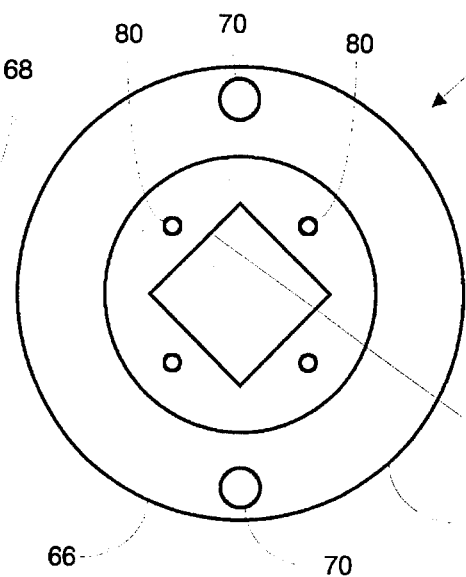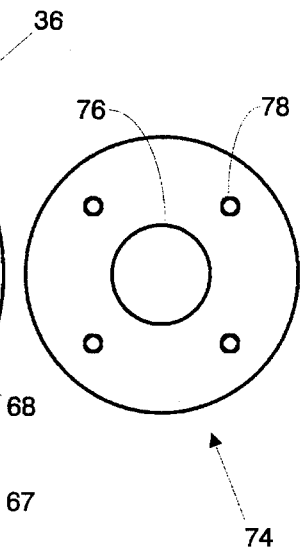
Fig. 7    Fig. 8    Fig. 9
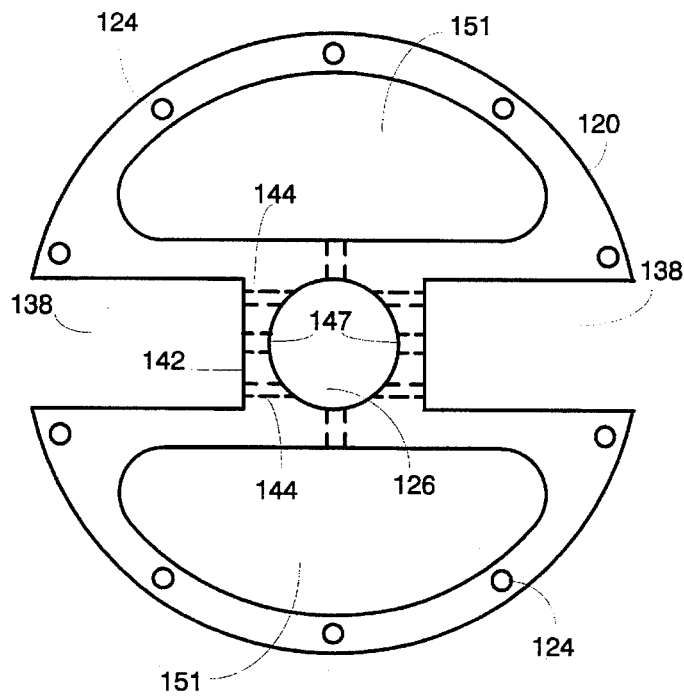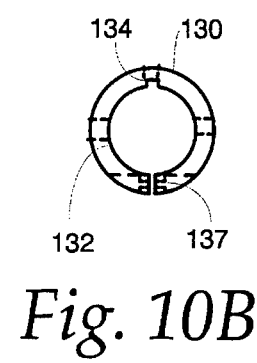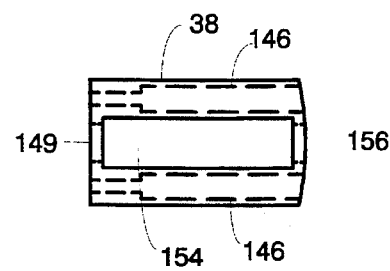
Fig. 10A    Fig. 10B    Fig. 10C

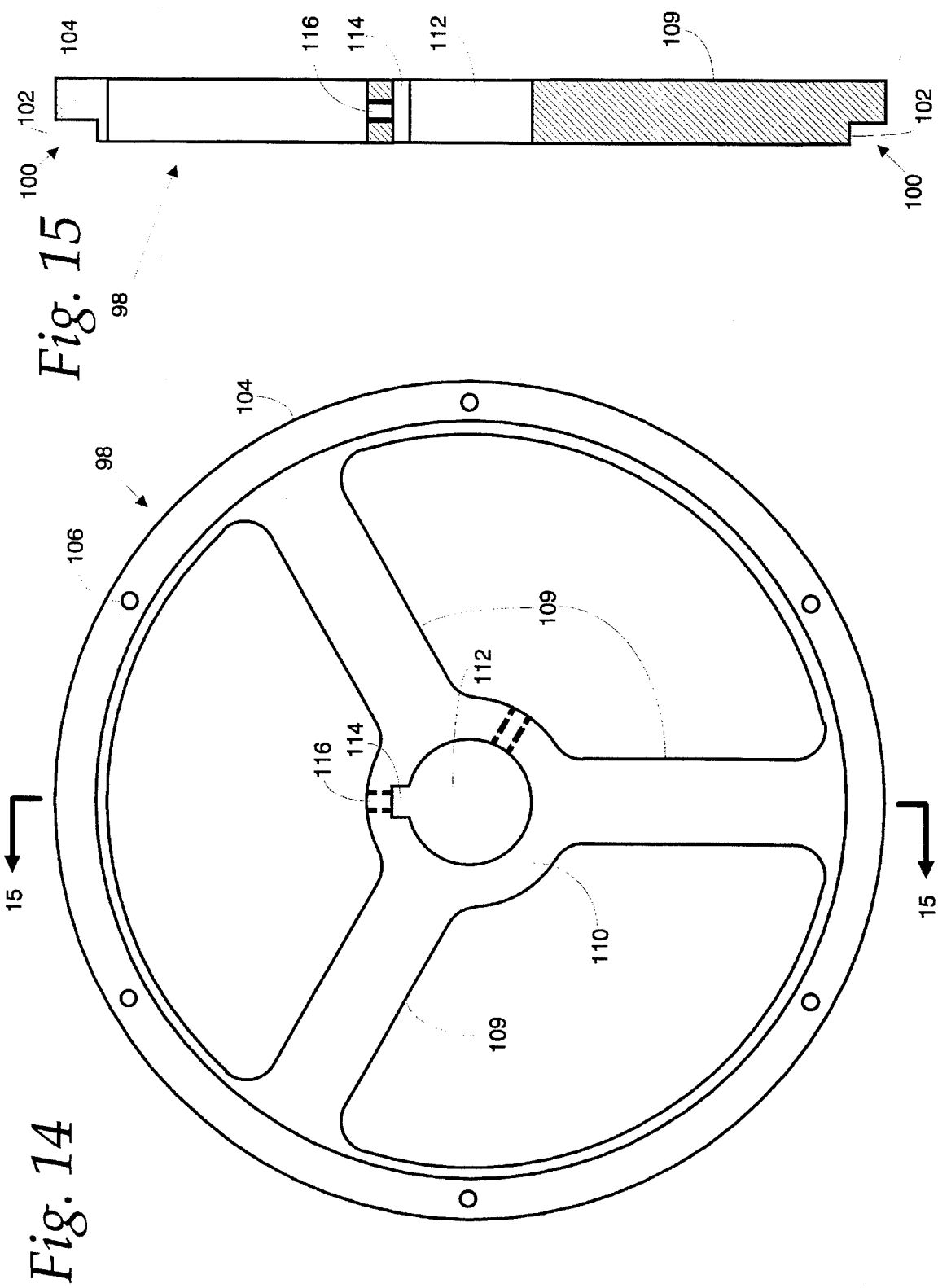

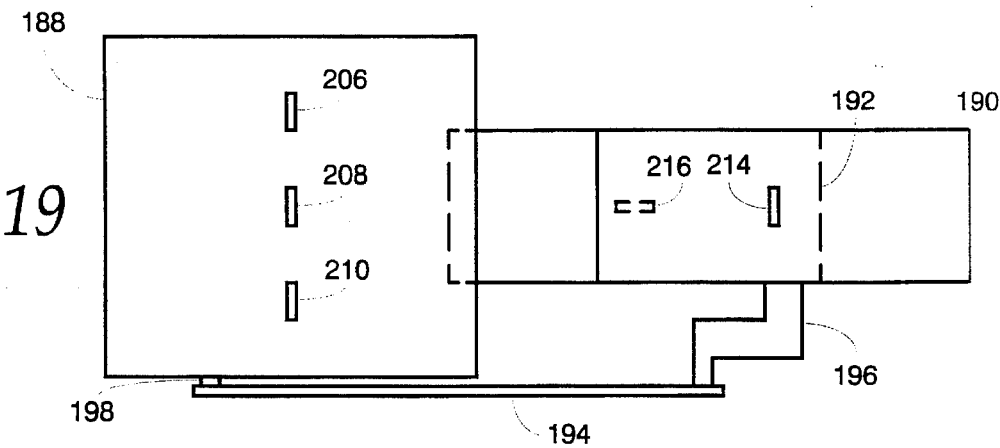
*Fig. 19*
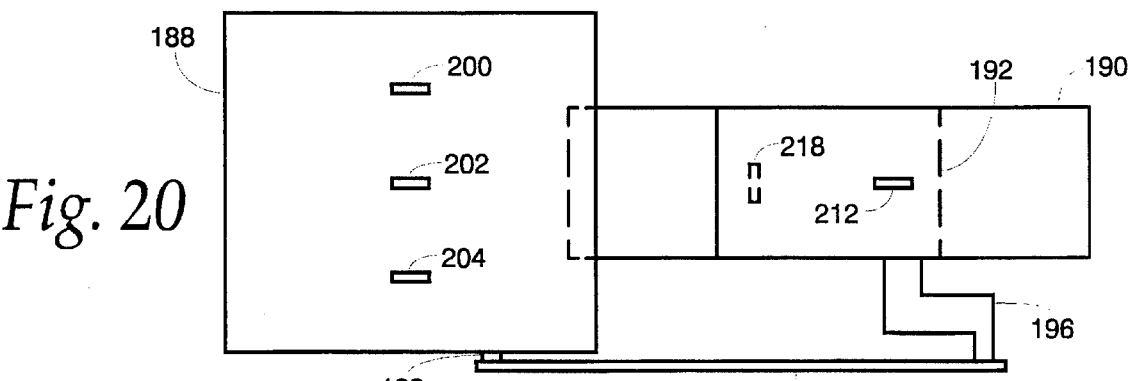
*Fig. 20*
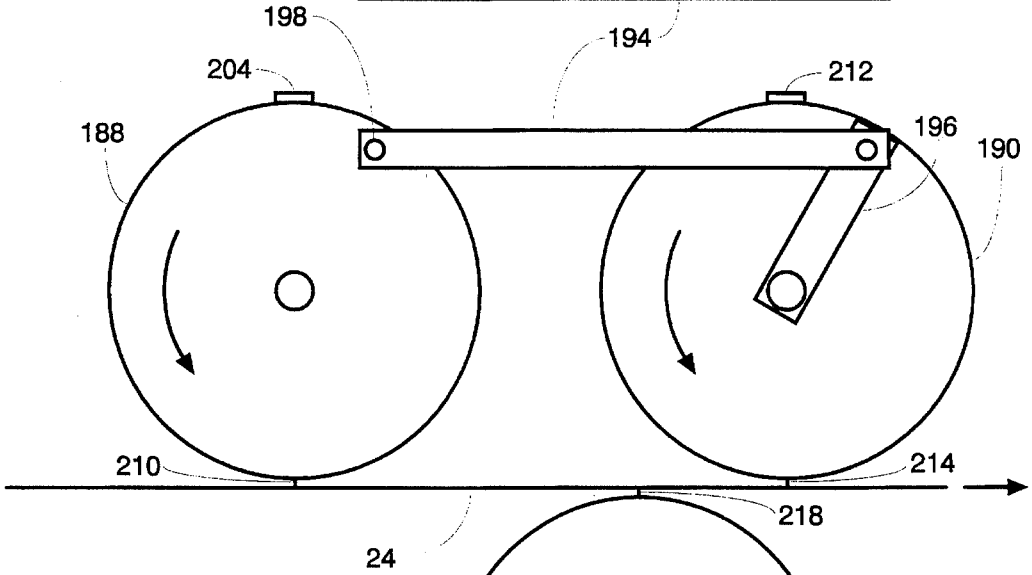
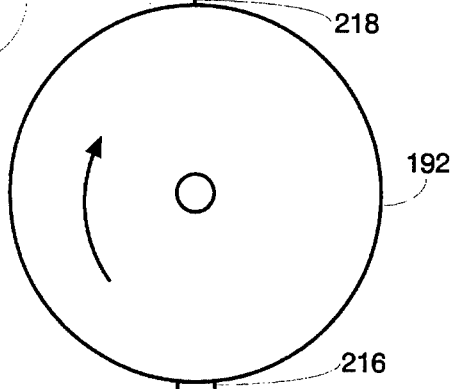
*Fig. 21*

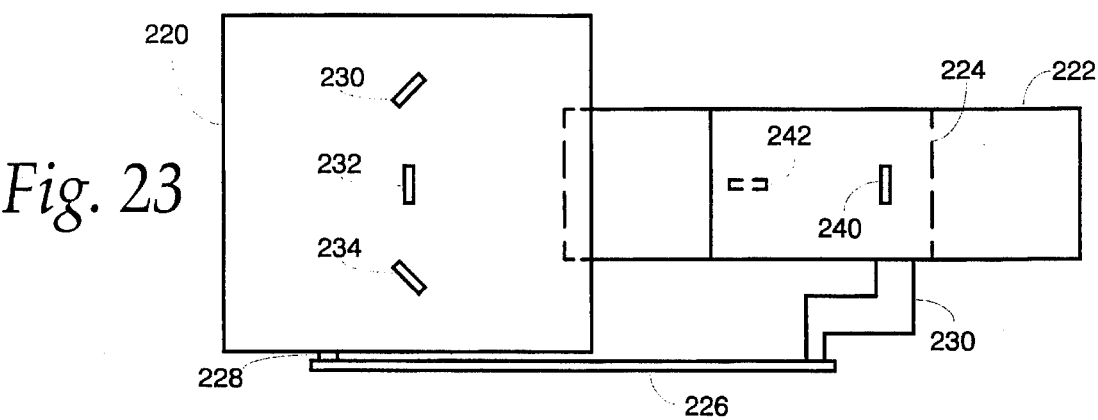
Fig. 23
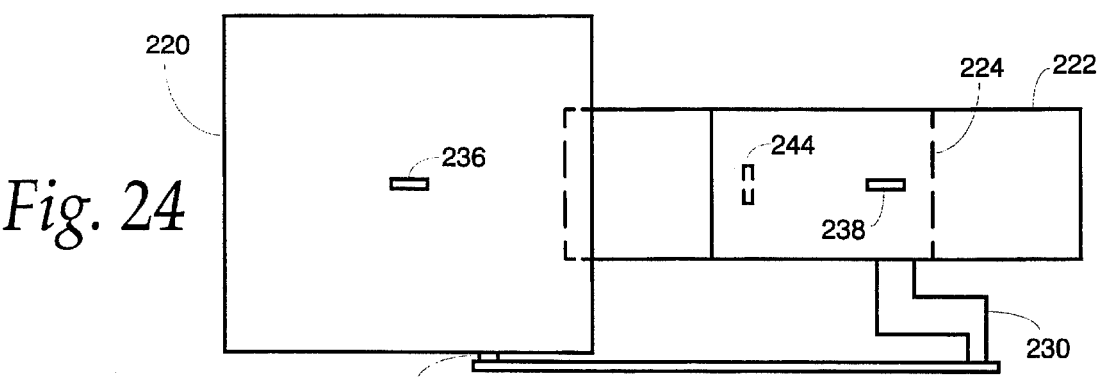
Fig. 24
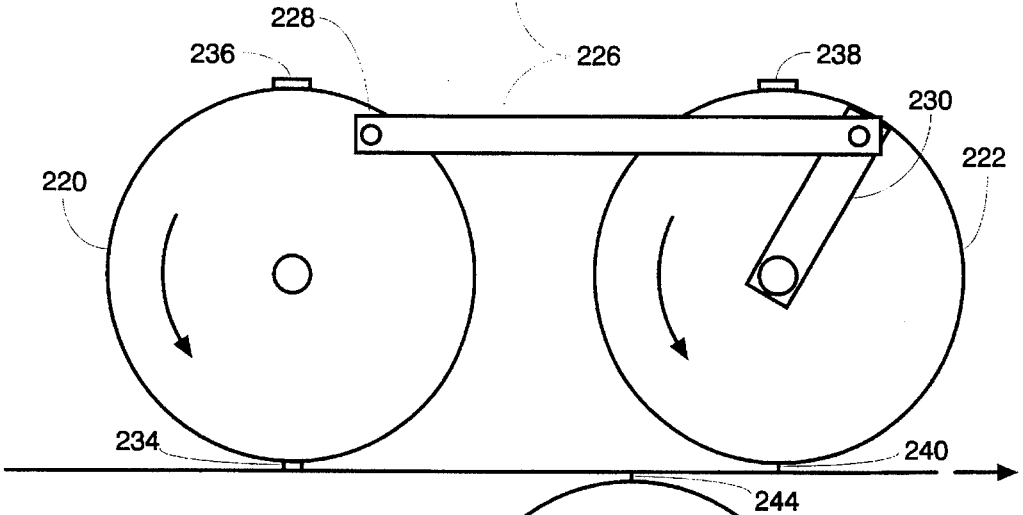
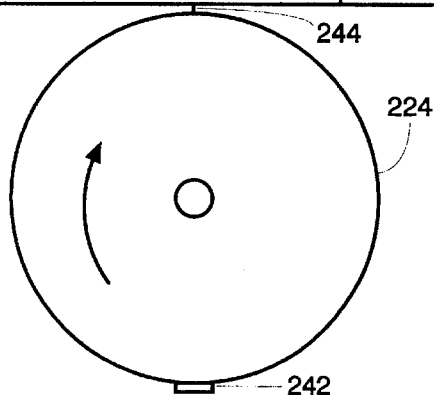
Fig. 25

IN-PLANE ULTRASONIC VELOCITY MEASUREMENT

This is a division of application Ser. No. 07/970,624, filed Nov. 3, 1992 now U.S. Pat. No. 5,493,910.

BACKGROUND OF THE INVENTION

1. Field of the Invention

The present invention relates to a system for improving the accuracy of non-destructive and non-intrusive testing techniques of moving web-like materials, such as paper, paperboard and other porous materials produced by the paper industry and, in particular, a system for improving the measurement of the velocity of ultrasonic signals in the plane of a moving web.

2. Description of the Prior Art

Web-like materials, such as paper, paperboard and the like are required to meet particular mechanical property specifications. Normal quality control techniques require that the web-like materials be tested to insure that the web uniformly meets the desired mechanical property specifications.

Destructive-type tests are known for measuring mechanical properties of such web-like materials. Such destructive tests are normally conducted off-line on representative samples of such web-like materials. There are various problems with such off-line destructive testing techniques. For example, such testing is relatively time consuming and requires production to be stopped or sampled periodically when product is received from the machine. In addition, since such testing is destructive, it is normally performed on representative samples of the web which may be taken, for example, every several thousand square feet of material. In such a situation, a substantial amount of waste is incurred if the web-like material is found to fail the test.

In order to solve the problems associated with such destructive test-type measurements of mechanical properties of web-like materials, ultrasonic testing techniques have been developed. Such testing is done on-line and thus is relatively quicker than off-line destructive testing, while at the same time provides a relatively continuous indication of various mechanical properties of the web-like material to assure virtually uniform quality of the product while minimizing waste.

Both in-plane and out-of-plane ultrasonic testing techniques are known for moving web-like materials. Out-of-plane ultrasonic testing relates to the measurement of the velocity of an ultrasonic signal through the thickness of the moving web-like material in order to determine various mechanical properties of the web. In such out-of-plane ultrasonic velocity measurement systems, ultrasonic transducers are normally disposed on opposing sides of the moving web. The velocity of the ultrasonic signal through the thickness of the web is measured in order to determine the mechanical properties of interest.

The velocity of an ultrasonic signal in the plane of the web is useful for determining certain mechanical properties of the web. Various systems are known for measuring the velocity of an ultrasonic signal in the plane of the web. In one system, such as disclosed in U.S. Pat. No. 4,730,492, a plurality of ultrasonic transducers are disposed along an outer surface of a hollow cylinder. As the transducers contact the web, the system measures the velocity of an ultrasonic signal in the plane of the moving web in both a longitudinal direction and a transverse direction relative to the web.

Although such systems may provide adequate measurement of ultrasonic signals in the plane of the web, there are problems with such systems. One problem with such a system relates to the variability of the contact force between the transducers and the web. Since the contact force between the transducers and the web affects the acoustical coupling therebetween, it is desirable that the contact force be relatively constant. However, various factors are known to affect the contact force including the manner in which the transducers are mounted to a rotating wheel or cylinder that carries the transducers. In known systems, the transducers are rigidly mounted relative to the cylinder or wheel. With such a system, adjustment of the transducers relative to the wheel or cylinder in order to adjust the contact force has been relatively difficult, often requiring the removal of the wheel or cylinder, making the adjustment of the transducers relatively difficult and time consuming.

Another problem with such a system is that the cylinder or wheels are known to depend upon friction to move at the speed of the web. As such, the web is partially wrapped about the cylinder or wheel. There are several problems with such friction-driven systems. For example, in such a system, an inertial load is placed on the web. As such, it would not be usable for certain products, such as relatively thin papers and tissues. Additionally, such friction-driven systems are known to cause undue wear to the transducers resulting from web to transducer speed differences. Moreover, ultrasonic signals in such a system may simultaneously propagate through the cylinder resulting in unpredictable interference at the ultrasonic receivers causing errors in the velocity measurements.

Moreover, such systems as described above are generally not suitable for use with relatively wide webs (e.g., webs wider than the length of the cylinder). In such applications, it is known to use a system, for example, as disclosed in U.S. Pat. No. 4,291,577. In that system, a pair of friction-driven, axially aligned wheels are disposed on one side of a moving web. Transducers disposed in the peripheral surface of the wheels enable the velocity of ultrasonic signals in the plane of the web to be measured. However, with such a system, it is relatively difficult to maintain good contact between the transducers and the web since the web tension decreases near the edges.

There are other problems with such in-plane ultrasonic testing systems. More particularly, known in-plane ultrasonic testing systems are adapted to provide an on-line indication of various properties of a moving web which depend on the velocity of ultrasonic signals in a machine direction (e.g., MD, the direction of travel of the moving web) and a cross-direction (e.g., CD, perpendicular to the machine direction). However, some useful mechanical properties of web-like materials depend on velocity measurements in directions other than the MD and the CD. For example, in-plane polar specific stiffness measurements require velocity measurements along successive axes, 5°–10° apart. As such, such measurements must be made off-line.

SUMMARY OF THE INVENTION

It is an object of the present invention to solve the problems associated with the prior art.

It is another object of the present invention to provide an improved system for measuring the velocity of ultrasonic signals in the plane of a moving web of paper-like material.

It is yet a further object of the present invention to provide a system for allowing continuous measurements of mechanical properties of moving web-like materials, such as the polar specific stiffness of the web.

It is yet another object of the present invention to provide a system for measuring the velocity of ultrasonic signals in the plane of the web which enables the contact force between the ultrasonic transducers and the web to be maintained relatively constant.

It is yet another object of the present invention to provide a system for measuring the velocity of ultrasonic signals in the plane of a moving web which eliminates inertial loading of the moving web.

It is yet a further object of the present invention to provide a system for measuring the velocity of an ultrasonic signal in the plane of the web which utilizes ultrasonic transducers disposed on opposing sides of the moving web.

It is a further object of the invention to reduce transducer wear due to friction.

Briefly, the present invention relates to an improved system for measuring the velocity of ultrasonic signals in the plane of moving web-like materials, such as paper, paperboard and the like. In addition to velocity measurements in the plane of the web in the MD and CD, one embodiment of the system in accordance with the present invention is also adapted to provide on-line indication of the polar specific stiffness of the moving web. In another embodiment of the invention, the velocity of ultrasonic signals in the plane of the web is measured by way of a plurality of ultrasonic transducers carried by synchronously driven wheels or cylinders, thus eliminating undue transducer wear due to any speed differences between the transducers and the web. The transducers are carried by transducer carrier assemblies, rigidly secured to the wheels or cylinders. The transducer carrier assemblies include springs for biasing the transducer radially outwardly to provide a relatively constant force relative to the webs. The transducer carrier assemblies are further adapted to be easily and conveniently mounted to a rotatably mounted wheel or cylinder relatively quickly and easily without the need to remove the cylinder or wheel from the test apparatus.

BRIEF DESCRIPTION OF THE DRAWING

These and other objects of the present invention will become readily understood with reference to the following specification and attached drawing, wherein:

FIG. 7 is an elevational view of a transducer carrier in accordance with the present invention;

FIG. 8 is an end view of the transducer carrier illustrated in FIG. 7;

FIG. 9 is an end cap for use with the transducer carrier illustrated in FIGS. 7 and 8;

FIG. 10A is a plan view of a transducer carrier disc in accordance with the present invention;

FIG. 10B is a plan view of a hub for use with the transducer carrier disc illustrated in FIG. 10A;

FIG. 10C is a plan view of an alternative embodiment of the transducer carrier illustrated in FIGS. 7–9;

FIG. 14 is a plan view of an end plate for closing the ends of the cylinder illustrated in FIGS. 12 and 13;

FIG. 15 is a cross-sectional view taken along line 15—15 of FIG. 14;

FIG. 19 is a top view of an alternate embodiment of the synchronous drive system illustrated in FIGS. 16–18, shown at 0° rotation with the shear transducers in contact with the web;

FIG. 20 is similar to FIG. 19 shown rotated 180° with the longitudinal transducers in contact with the web;

FIG. 21 is an elevational view of the system illustrated in FIGS. 19 and 20, shown with the longitudinal transducers in contact with the web;

FIG. 23 is a plan view of another alternate embodiment of the synchronous drive system illustrated in FIGS. 16–18 shown at 0° rotation with the shear transducers in contact with the web;

FIG. 24 is similar to FIG. 23 shown at 180° rotation with the longitudinal transducers and two 45° transducers in contact with the web;

FIG. 25 is an elevational view of the system illustrated in FIGS. 23 and 24, shown with the longitudinal and 45° transducers in contact with the web;

DETAILED DESCRIPTION OF THE PREFERRED EMBODIMENT

Figure 1:
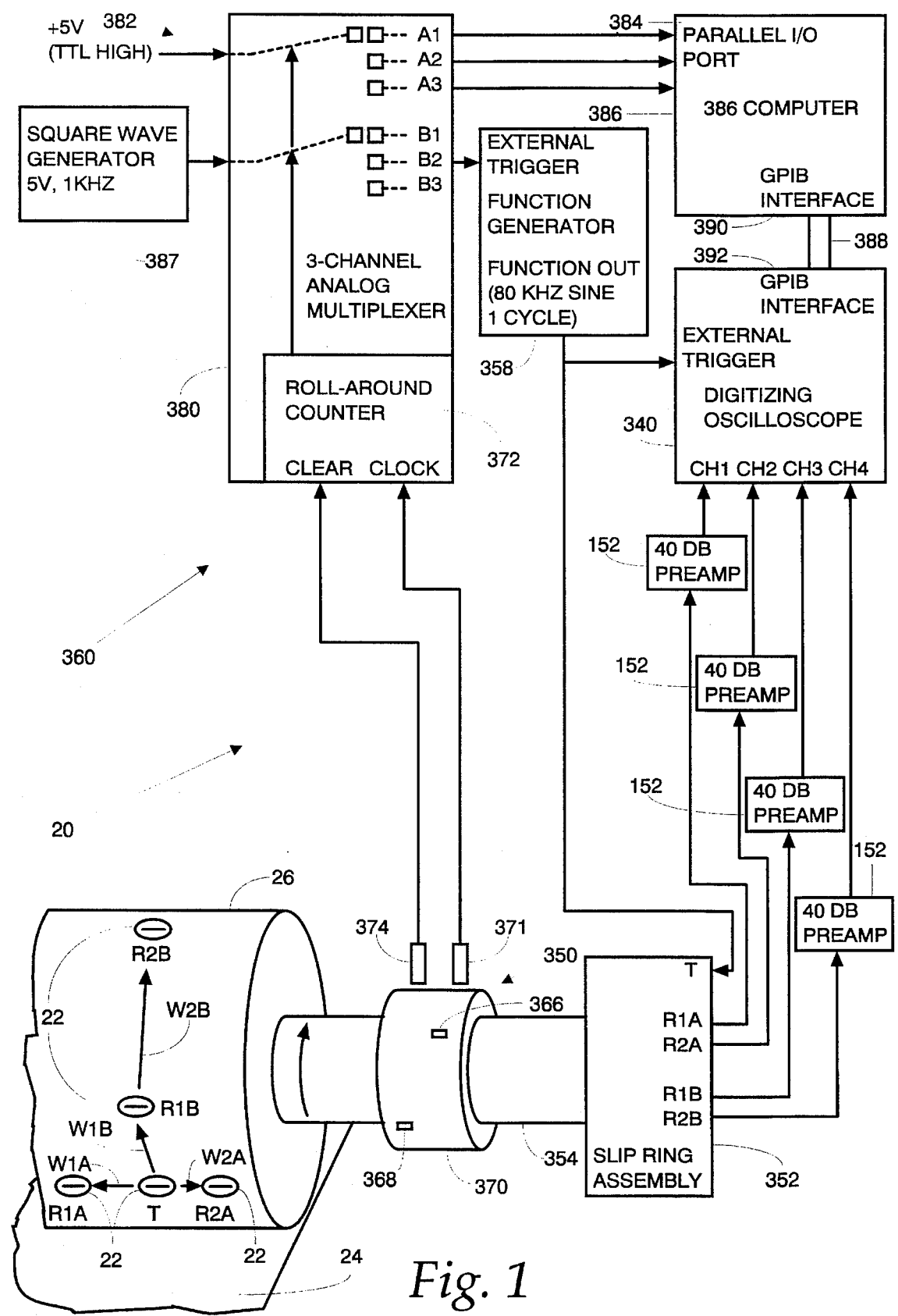
FIG. 1 is a block diagram of one embodiment of an ultrasonic testing system in accordance with the present invention.
Figure 16:
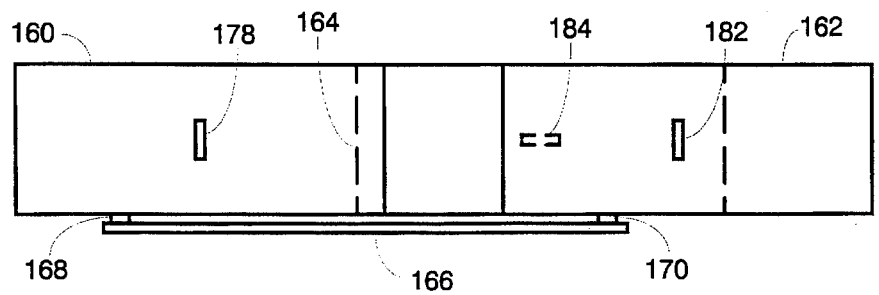
FIG. 16 is a top view of a synchronous drive system in accordance with the present invention shown at 0° rotation with the shear transducers in contact with the web.
Figure 17:
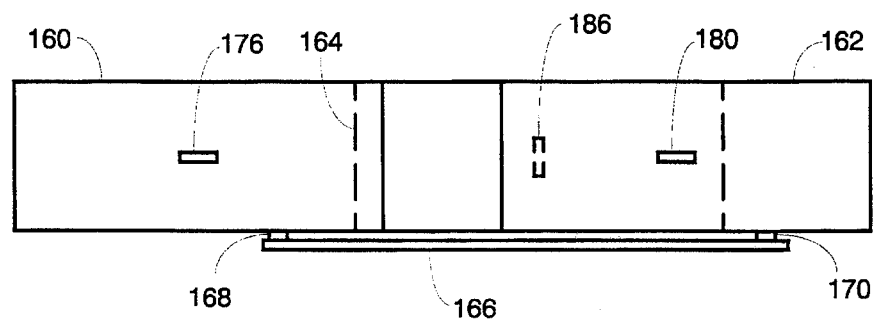
FIG. 17 is similar to FIG. 16 shown rotated 180° with the longitudinal transducers in contact with the web.
Figure 18:
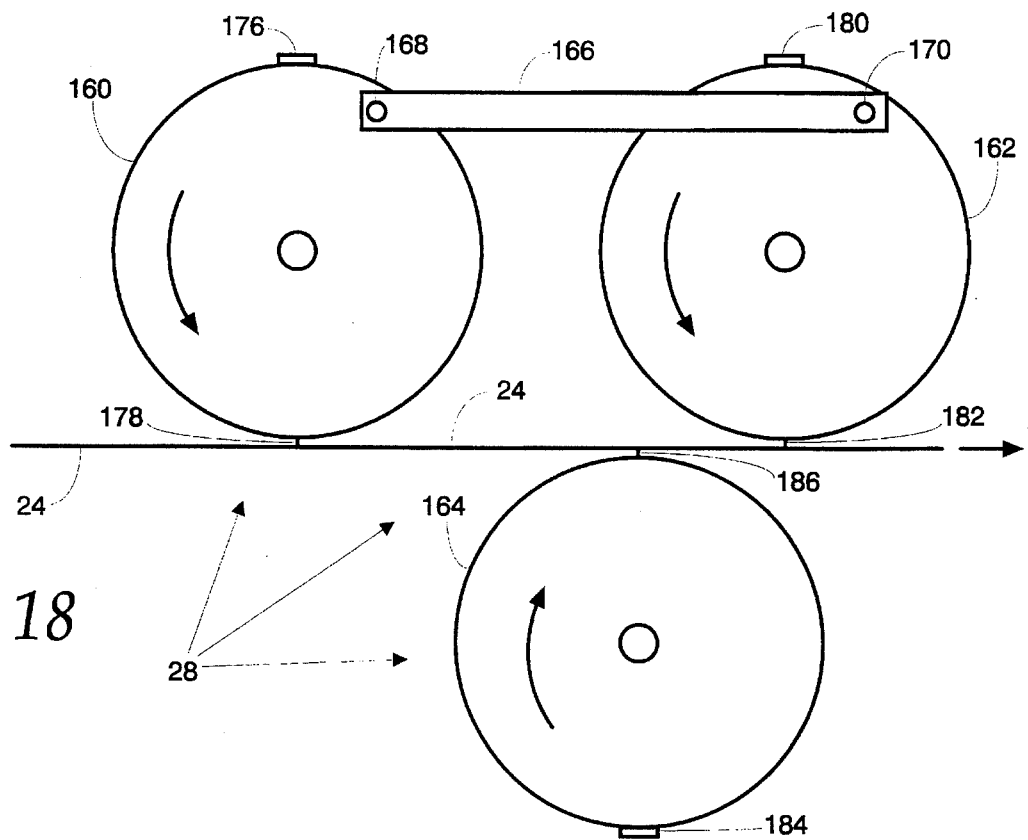
FIG. 18 is an elevational view of the system illustrated in FIGS. 16 and 17 shown with the longitudinal transducers in contact with the web.

One embodiment of a system in accordance with the present invention for measuring the velocity of ultrasonic signals in the plane of moving web-like materials, such as paper, paperboard and other porous materials produced by the paper industry, is generally illustrated in FIG. 1 and identified with the reference numeral 20. The system 20 includes a plurality of ultrasonic transducers, generally identified with the reference numeral 22, disposed adjacent a moving web 24. In the embodiment of the invention illustrated in FIG. 1, the transducers 22 are carried by a rotating cylinder 26, disposed to be in contact with one side of the moving web 24. In an alternate embodiment of the invention, for example, as illustrated in FIGS. 16–18, the transducers 22 are carried by rotatably mounted wheels, generally identified with the reference numeral 28. The alternate embodiment is used in applications for relatively wider webs (e.g., webs generally wider than the length of the cylinder 24). In addition, various drive systems are disclosed.

In all embodiments of the invention, a relatively constant contact force between the transducers 22 and the moving web 24 is maintained. In order to provide such a relatively constant contact force, the transducers 22 are carried by transducer carrier assemblies 29 (FIG. 6) and 30 (FIG. 11) which, in turn, are mounted to either the cylinder 26 (FIGS. 12 and 13) or carried by the wheel assembly 28 (FIG. 11), respectively. The transducer carrier assemblies 29, 30 include biasing springs 32 for biasing the transducers 22 outwardly. As such, a relatively constant contact force will be maintained between the web 24 and the transducers 22.

Another important aspect of the invention relates to the drive system for the cylinder 26 and the wheel assemblies 28. In known ultrasonic testing systems, for example, as disclosed in U.S. Pat. Nos. 4,291,577 and 4,730,492, the cylinders and wheels are friction driven. More specifically, in such systems, the web is partially wrapped about either the cylinder or wheels to provide a friction drive. However, such systems can cause undue wear to the transducers resulting from the friction due to web- to-transducer speed differences. Moreover, such friction-driven systems place an inertial load on the web and thus are not suitable for certain materials, such as relatively thin webs and tissue. As mentioned above, one embodiment of the system in accordance with the present invention solves these problems by providing an independent drive system for the cylinder 26 or wheel assemblies 28, synchronized to the web speed, thereby minimizing undue wear to the transducers due to web-to-transducer speed differences.

Another important aspect of the invention relates to the configuration of the transducers 22 in order to enable certain important mechanical properties of the web to be measured while the web 24 is moving. More particularly, in one embodiment of the invention (FIGS. 23–25), several of the transducers 22 are oriented at 45° angles with respect to the MD. This enables the system in accordance with the present invention to provide on-line indication of the polar specific stiffness of the web.

Transducer Carrier Assemblies

An important aspect of the invention relates to transducer carrier assemblies 29 (FIG. 6) and 30 (FIG. 11) for use with a rotating cylinder 26 (FIGS. 12 and 13) and the rotating wheel assemblies 28 (FIG. 11), respectively. These assemblies 29 and 30 are adapted to be rigidly assembled to the cylinder 26 and wheel assemblies 28, respectively, without the need to remove the cylinder 26 or wheels 28 through 40 from the system. Thus, replacement and adjustment of the transducers 22 through 30 is relatively quick and easy. Moreover, as will be discussed in more detail below, the transducer carrier assemblies 29 and 30 bias the transducers 22 radially outwardly thereby providing a relatively constant contact force between the transducers 22 and the web 24 which, in turn, provides substantially uniform acoustical coupling therebetween.

Figure 3:
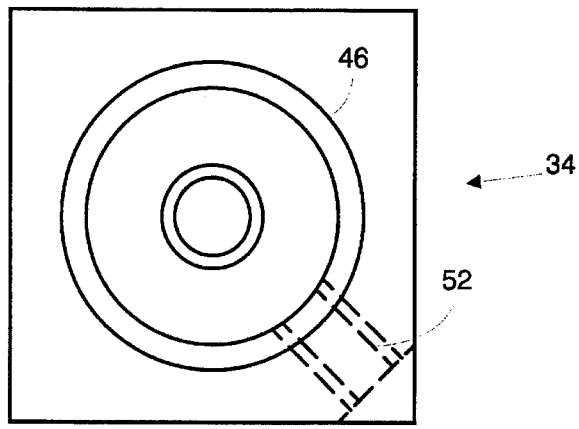
FIG. 3 is a plan view of the transducer housing illustrated in FIG. 2.
Figure 2:
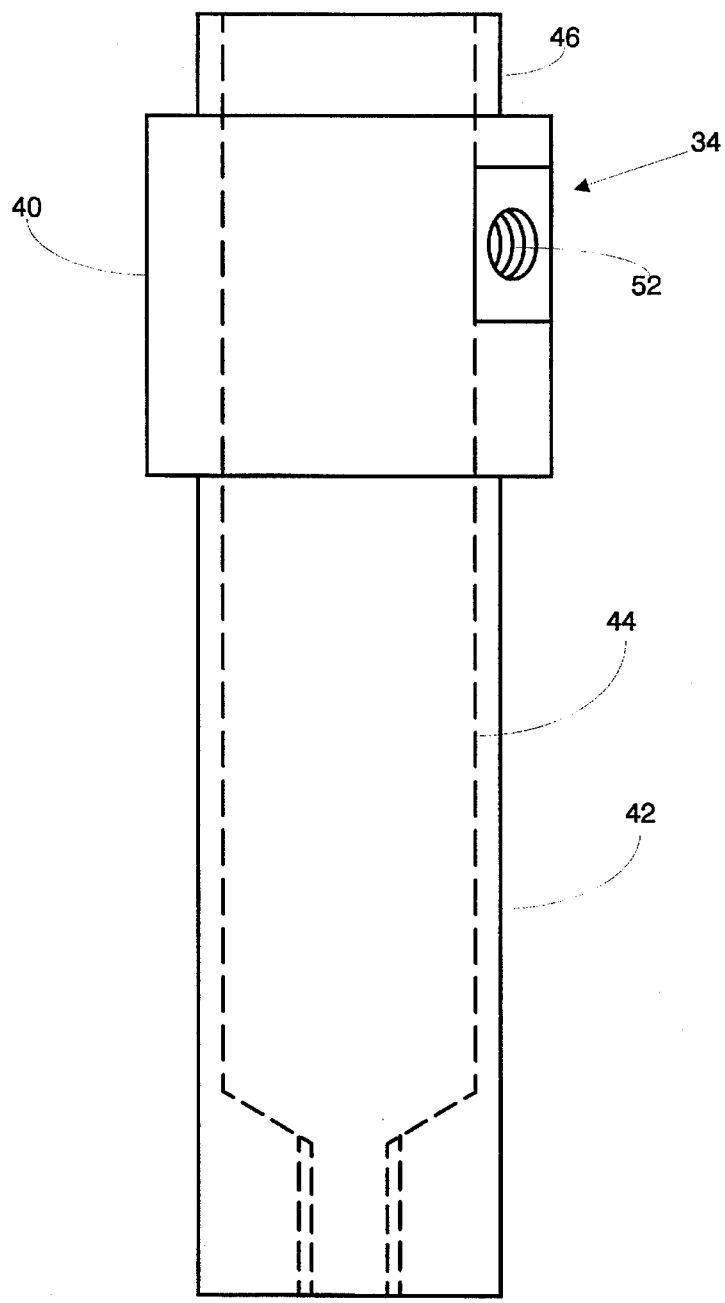
FIG. 2 is an elevational view of a transducer housing in accordance with the present invention.
Figure 6:
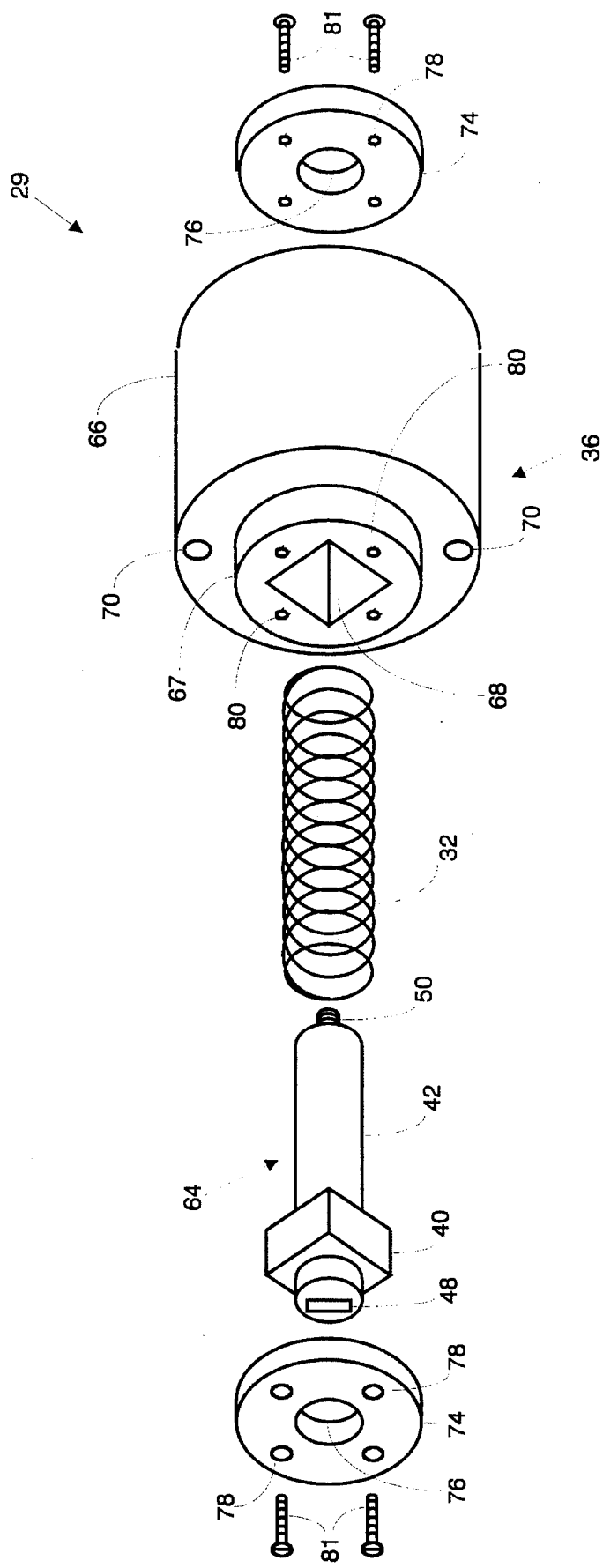
FIG. 6 is an exploded perspective view of one embodiment of a transducer carrier assembly in accordance with the present invention.
Figure 11:
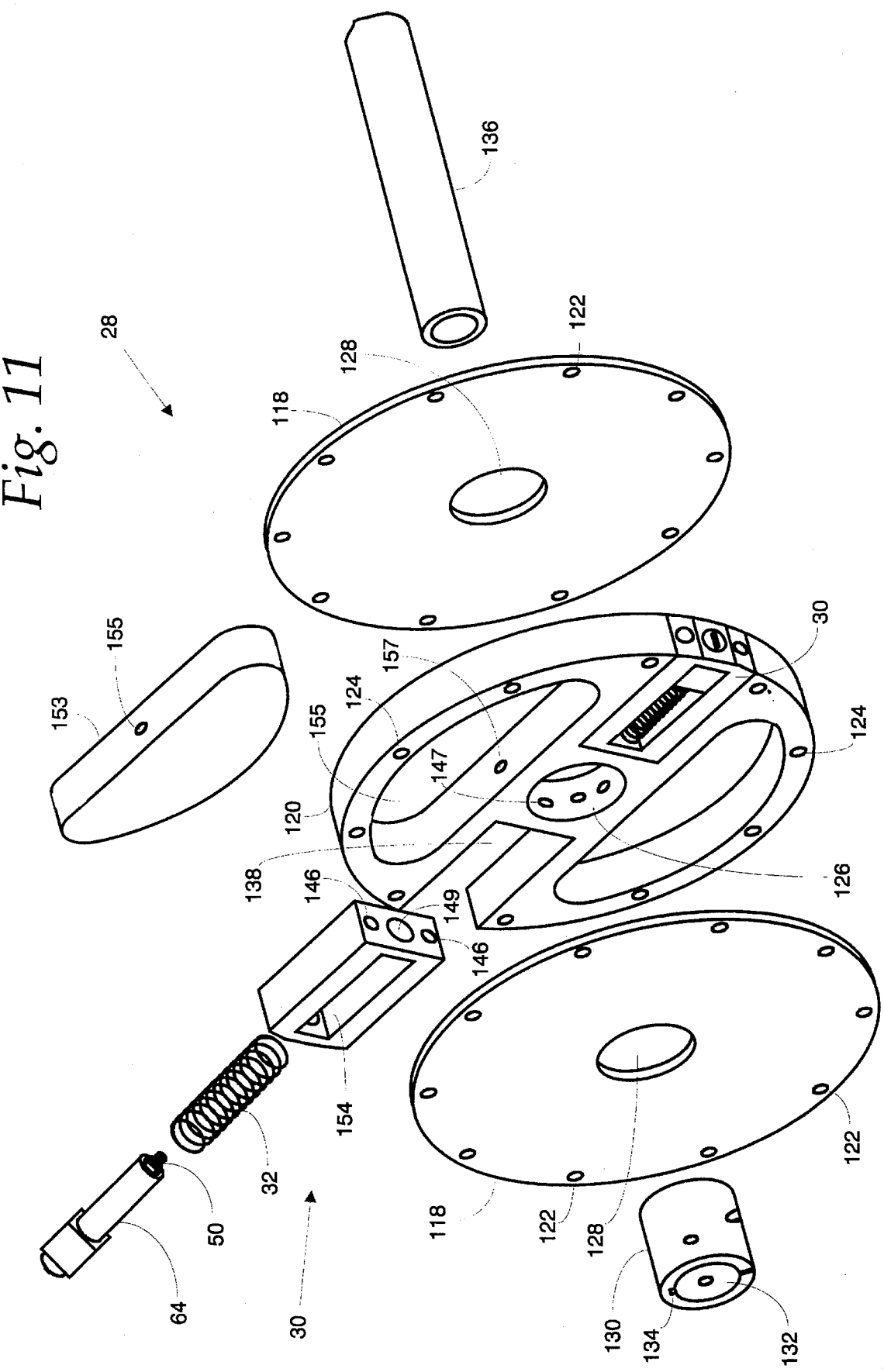
FIG. 11 is an exploded perspective view of the wheel assembly and an alternate embodiment of the transducer carrier assembly illustrated in FIG. 6 in accordance with the present invention.

The transducer carrier assemblies 29 and 30 include transducer carriers 36 (FIGS. 7–9) and 38 (FIG. 10C), respectively, a transducer housing 34 (FIGS. 2 and 3) and a biasing spring 32 (FIGS. 6 and 11). The transducer housing 34 carries the transducers 22, preferably a wide-band, bimorph, bender transducer. Such transducers 22 are described in detail in "*Using a Robot-Based Instrument to Measure In-Plane Ultrasonic Velocities of Paper*", by C. C. Habeger, M. L. Van Zummeren, W. A. Wink, B. M. Pankonin and R. S. Goodlin, *Tappi Journal*, Jul. 1989, pp. 171–175, herein incorporated by reference. In particular, the transducer housing 34, preferably formed from aluminum, includes a first portion 40 formed with a generally square cross section and an integrally formed second portion 42 with a generally circular cross section. A central bore 44, tapered at one end, extending the entire length of the housing 34, is adapted to receive the transducers 22. Another circular portion 46 is integrally formed adjacent the first portion 40 of the housing 34 and is adapted to surround an electrode (ceramic bimorph) 48 (FIG. 6) on the transducer 22 and also acts as a guide surface when the transducer housing 34 is assembled to the transducer carriers 36 and 38, as will be discussed below. A threaded stud 50 (FIG. 6), which enables the transducer 22 to be connected to an electrical conductor (not shown), is adapted to extend outwardly from the opposing end of the transducer housing 34. The transducer housing 34 is further provided with a threaded radial hole 52 (FIGS. 2 and 3) for receiving a set screw (not shown) to enable the transducer 22 to be secured relative to the housing 34.

In order to provide a relatively durable wear surface for the transducers 22, a wear surface or nosepiece 54 (FIGS. 4 and 5) may be adhered to the electrode 48 (FIG. 6) of the transducers 22. An important aspect of the wear surface 54 in accordance with the present invention is the relatively easy manner in which it is made and attached to the electrode 48 in contradistinction to known nosepieces. More specifically, U.S. Pat. No. 4,713,572 discloses a nosepiece for protecting a transducer electrode. Such nosepieces are known to include bevelled or rounded edges. As such, such nosepieces are relatively expensive to manufacture. The nosepiece 54 in accordance with the present invention is formed from a grooved ring 56, illustrated in FIGS. 4 and 5. The grooved ring 56, preferably made from a brass rod, for example, is formed by drilling a hole 58 having a radius R1 into the exposed end of the rod with the use of a lathe (not shown). Subsequently, a tool bit (not shown) is positioned in the hole 58 and used to machine a groove 60 to a depth of radius R2. The radius R2 is selected to match the radius of a rounded end of the ceramic bimorph. The width of the groove 60 is selected to be slightly greater than the width of the electrode 48. After the groove 60 is machined, the outer surface of the rod is machined to a radius R3 with the lathe. The ring 56 is then cut off to the desired width to form the groove ring 56, illustrated in FIGS. 4 and 5.

Figures 4, 5:
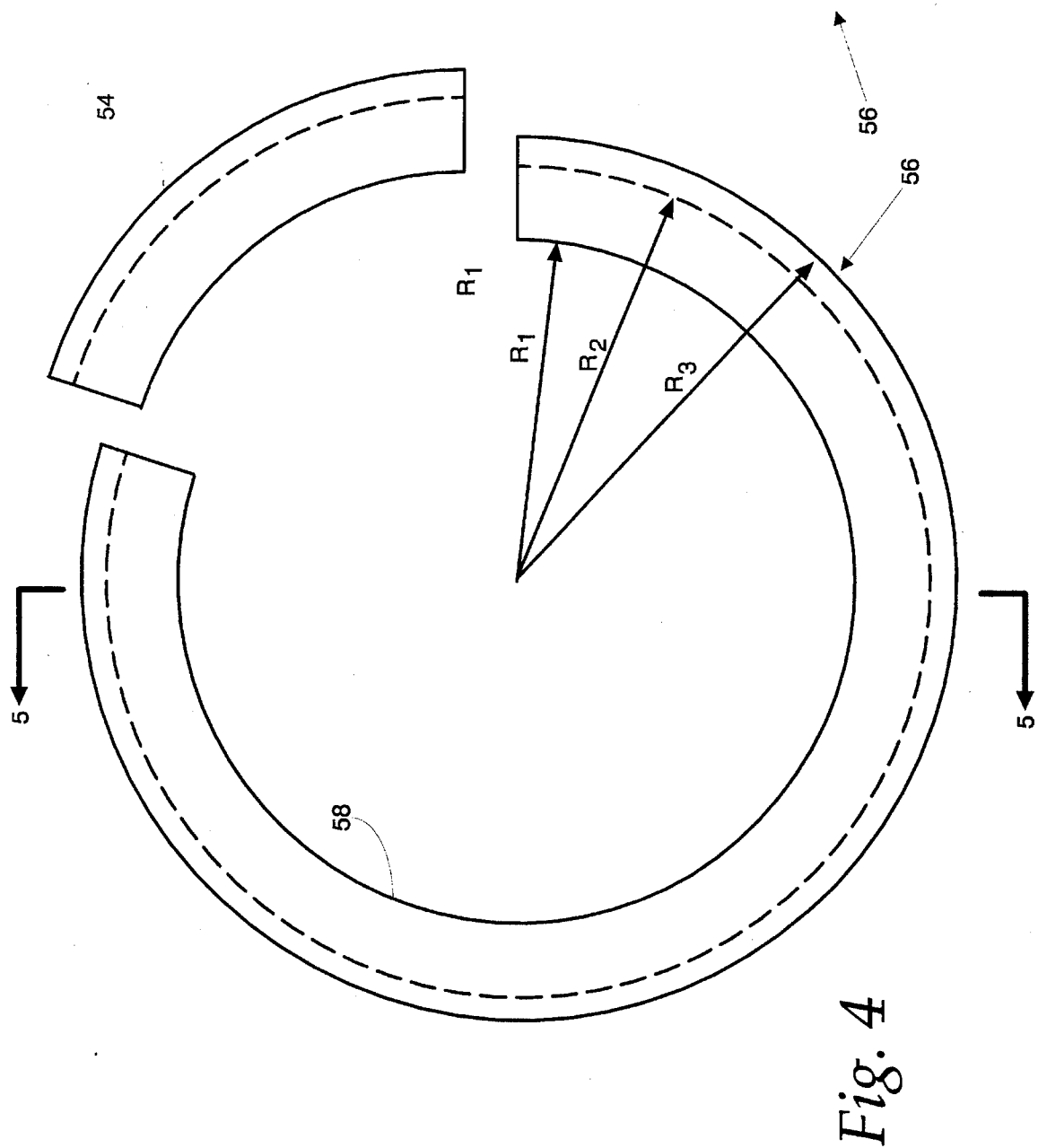
FIG. 4 is an elevational view of a grooved ring in accordance with the present invention.
FIG. 5 is a cross-sectional view along line 5—5 of FIG. 4.

Once the grooved ring 56 is formed, radial segments of the ring 56 are cut out, for example as illustrated in FIG. 4 to form the nosepiece 54. The size of the segment 54 is selected to cover the electrode 48 of the transducers 22. After segment 54 is cut, resulting burrs are removed with a file.

Prior to attaching the nosepiece 54 to the electrode 48, a thin layer of an electrically insulating adhesive, such as epoxy 907, is applied to the electrode 48 and allowed to cure. Finally, an electrically insulating adhesive is deposited in the groove 60. The electrode 48 is then pressed into the groove 60 and the assembly is allowed to cure. The transducer 22 and attached nosepiece 54 are then installed in the transducer housing 34 forming a transducer assembly 64 (FIGS. 6 and 11). The transducer assembly 64 is then ready for insertion into the transducer carriers 36 (FIG. 6) and 38 (FIGS. 10C).

It is also contemplated to form the nosepieces 54 from a length of piano wire. In such an embodiment, the piano wire is bent to the radius of the electrode. The formed piano wire is then attached to the electrode 48 in the manner discussed above.

The transducer carrier 36 is generally formed in a cylindrical shape having a cylinder portion 66 and a reduced diameter portion 67 (FIGS. 6–8), preferably from a plastic material, such as Ultra High Molecular Weight Polyethylene (UHMP). A generally square bore 68, sized to be slightly larger than the square portion 40 of the transducer housing 34, is formed along the length of the carrier 36 to enable the transducer housing 34 to slide freely therewithin. The reduced outer diameter portion 67 enables the transducer carrier 36 to be received in a counter bore 69 (FIGS. 12 and 13), formed in the cylinder 26.

A pair of diametrically opposed through holes 70 are provided to enable the transducer carrier 36 to be rigidly secured to the cylinder 26. In particular, once the transducer assembly 64 is assembled to the transducer carrier 36, the through holes 70 are aligned with tapped holes 72 (FIG. 12) formed in the cylinder 26. Suitable threaded fasteners (not shown) are then used to secure the transducer carrier 36 to the cylinder 26. The radial position of the through holes 70 relative to the bore 68 is selected to be in line with the corners of the square bore 68 as shown.

The cylinder portion 66 (FIGS. 6 and 8) of the transducer carrier 36 is open on both ends to enable the transducer assembly 64 to be relatively easily disposed therewithin. The ends of the cylinder portion 66 are closed with end plates 74 (FIG. 9). Prior to attaching the end plates 74, the biasing spring 32 is slipped over the circular portion 42 of the transducer housing 34. The transducer assembly 64 and biasing spring 32 are then inserted into the bore 68 in the cylinder portion 66 such that the electrode 48 is disposed adjacent the reduced diameter portion 67 of the carrier 36. The end plates 74 are then used to close the ends of the bore 68 to capture the transducer assembly 64 and biasing spring 32 therewithin.

Figure 12:
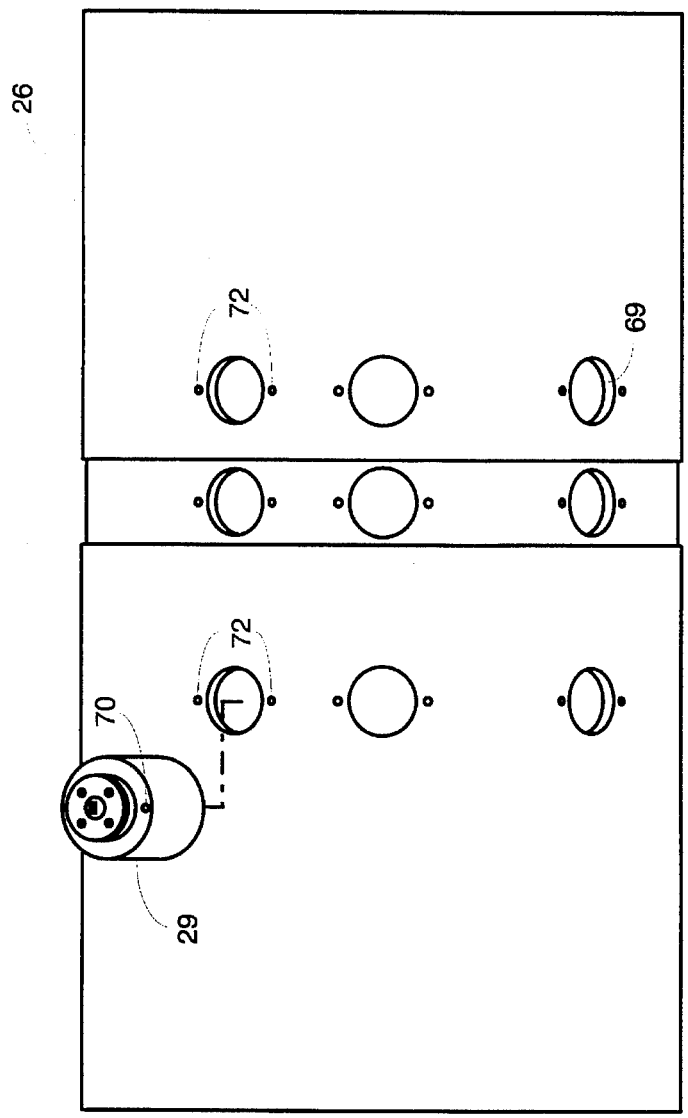
FIG. 12 is a plan view of a cylinder in accordance with the present invention shown with one transducer carrier assembly removed.

The end plates 74 are formed in a generally circular shape having a radius smaller than the radial distance of the through holes 70 on the cylinder portion 66. A centrally disposed aperture 76 is formed in the end plate 74 along with a plurality of radially spaced through holes 78. The central aperture 76 is sized to be slightly larger than the circular portion 46 formed on the transducer housing 34 to enable the circular portion 46 to be freely received therein. The central aperture 76 is also formed to be slightly larger than the outer diameter of the circular portion 42 of the transducer housing 34 to hold one end of the biasing spring 32 within the transducer carrier 36. The radially spaced holes 78 in the end plates 74 are adapted to be aligned with tapped holes 80 in the transducer carrier 36 to enable the end plates 74 to be secured to the carrier 36 with suitable threaded fasteners 81 to form the transducer carrier assembly 29 (FIG. 12).

Figure 13:
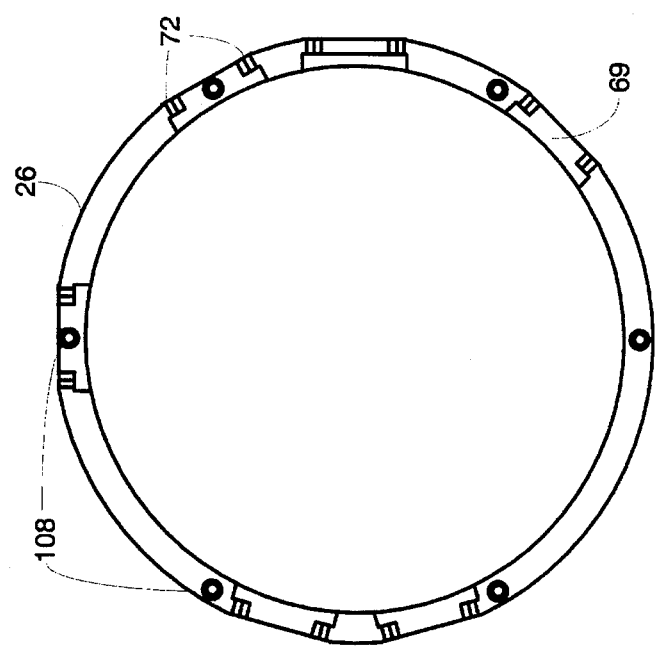
FIG. 13 is an end view of the cylinder illustrated in FIG. 10.

The transducer carrier assembly 29 is adapted to be quickly and easily assembled to the cylinder 26. In particular, the cylinder 26, shown in FIGS. 12 and 13, is preferably formed from aluminum as a hollow cylinder, open on both ends, with a plurality of counterbores 69, as discussed above, for receiving the transducer carrier assemblies 29. In particular, the transducer carrier assemblies 29 are inserted into the counter bores 69 from the inside of the aluminum cylinder 26. The through holes 70 on the transducer carrier assemblies 29 are aligned with tapped holes 72 in the cylinder 26 to enable the transducer carrier assemblies 29 to be rigidly secured to the cylinder 26 with suitable threaded fasteners (not shown). Thus, with such an arrangement, the transducer assemblies 29 can be relatively quickly and easily assembled and disassembled from the cylinder 26 without the need to remove the cylinder 26.

The ends of the hollow cylinder 26 are closed with end caps 98 (FIGS. 14–15). The end caps 98 are formed with an annular step 100 having a reduced diameter portion 102 and an annular flange portion 104. The reduced diameter portion 102 is received in the inner diameter of the cylinder 26. The annular flange 102 is provided with a plurality of radially spaced through holes 106 to enable the end caps 98 to be aligned tapped holes 108 (FIG. 13) in the cylinder 26 and secured thereto with suitable threaded fasteners (not shown).

The end caps 98 (FIGS. 14 and 15) are formed with a plurality of spokes 109 joined together at an integrally formed central hub 110. The hub 110 is formed with a central bore 112 which includes an integrally formed keyway 114 to enable the cylinder 26 to be connected to a drive system (not shown). The keyway 114 may be formed with a tapped hole 116 for receiving a set screw (not shown) for securing a key (not shown) relative to the keyway 114.

The transducer carrier assembly 30 for use with the wheel assemblies 28 is illustrated in FIG. 11. In particular, FIG. 11 illustrates an exploded perspective of one of the wheel assemblies 28 including a transducer carrier assembly 30, shown with one assembled transducer carrier assembly 30 secured thereto.

Each of the wheel assemblies 28 includes a pair of end plates 118 and a carrier disc 120, adapted to be sandwiched therebetween. Each of the end plates 118 include a plurality of radially-spaced through holes 122. The through holes 122 are adapted to be aligned with tapped holes 124 in the carrier disc 120 to allow the end plates 118 to be secured to the carrier disc 120 by suitable threaded fasteners (not shown). The carrier disc 120 as well as the end plates 118 are formed with central bores 126 and 128 respectively. These bores 126 and 128 are adapted to receive a hub 130 which includes a central bore 132 and a keyway 134 for receiving a hollow drive shaft 136. The hub 130 may be coupled to the end plates 118 and the carrier disc 120 by various means to prevent rotation of the hub 130 relative to the end plates 118 and carrier disc 120. For example, the hub 130 may be formed as a split ring and include a clamping mechanism 137 (FIG. 10B) for clamping the split ring relative to the drive shaft 136 to prevent rotational and axial movement of the hub 130 relative to the drive shaft 136.

The carrier disc 120 (FIG. 10A) is formed as a generally flat disc which includes one or more radially spaced cutouts 138 for receiving the transducer carrier assemblies 30. As shown, two generally rectangular or U-shaped cutouts 138 are provided, radially spaced apart by 180°. Each cutout 138 is formed to be slightly larger than a transducer carrier assembly 30.

The transducer carrier assembly 30 (FIG. 11) includes the transducer carrier 38 and is adapted to be rigidly connected to the carrier disc 120. In particular, a bight portion 142 (FIG. 10A) of the cut out 138 is provided with a plurality of tapped holes 144 (FIG. 10A). The tapped holes 144 are adapted to be aligned with through holes 146 formed in the transducer carrier 38 (FIG. 10C) to enable the transducer carrier 38 and thus the transducer carrier assembly 30 to be rigidly secured to the carrier disc 120 by way of suitable threaded fasteners (not shown).

Figure 26:
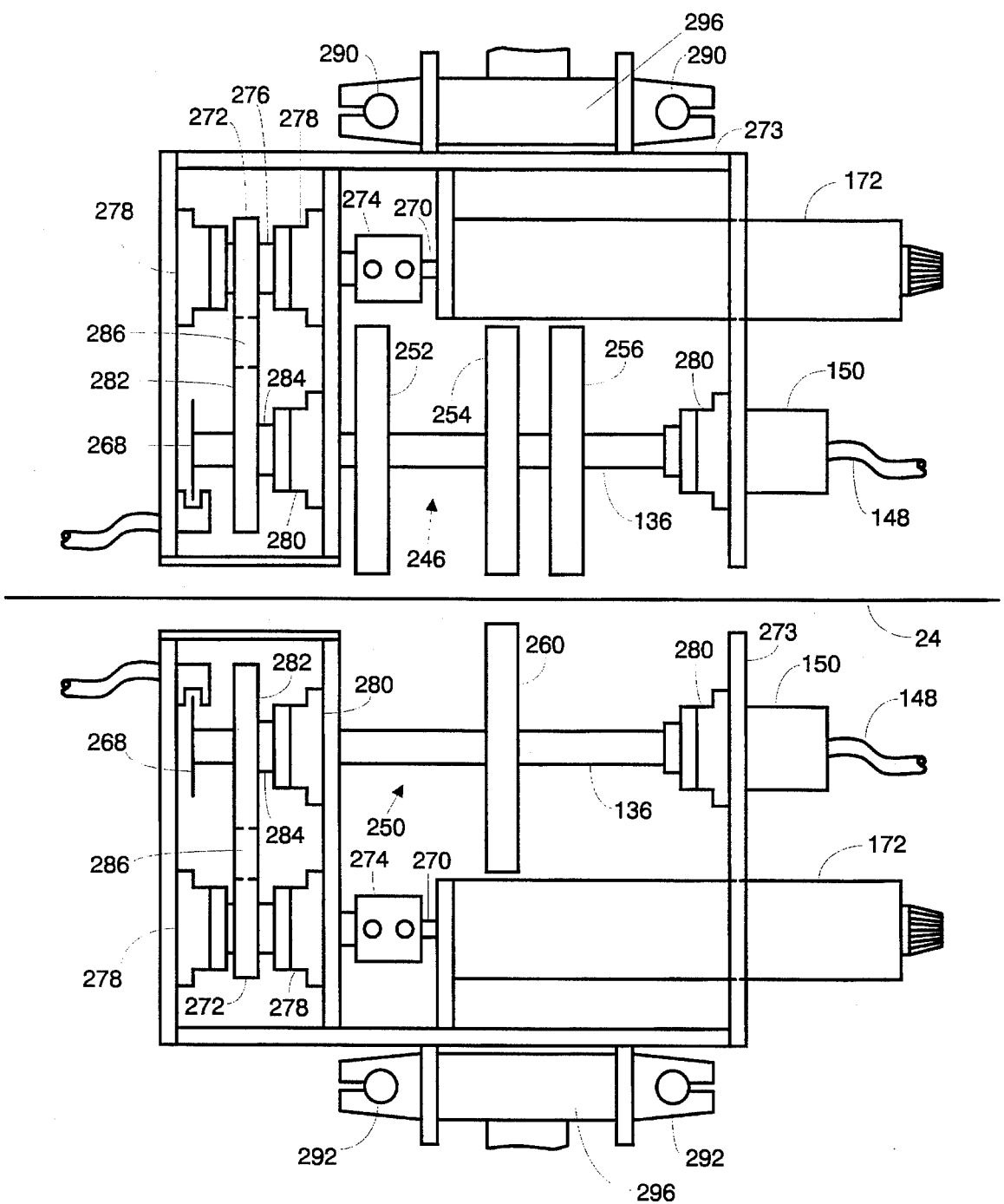
FIG. 26 is an elevational view of an ultrasonic testing system in accordance with the present invention, shown looking in the direction that the web is moving.

A radial bore 147 (FIG. 10A) is formed between the bight portion 142 and the central bore 126 of the carrier disc 120 forming a conduit for an electrical conductor 148 (FIG. 26). A bore 149 (FIG. 10C) is also formed on one end of the transducer carrier 38, adapted to be aligned with the bore 147 on the transducer disc 120, to allow the threaded stud 50 (FIG. 11) on the transducer assembly 64 to be connected to the electrical conductor 148 and routed through the hollow drive shaft 136 and connected to a slip ring assembly 150 (FIG. 26).

The carrier disc 120 may also be formed with one or more arcuate cut outs 151 (FIGS. 10A and 11). The arcuate cut outs 151 may be used, for example, to house electrical components, for example, preamplifiers 152 (FIG. 1) for the transducers 22. In particular, a preamp housing 153 (FIG. 11) is formed to the same contour as the arcuate cut out 151. The preamp housing 153 may be opened on one or both ends to enable the preamp 152 to be inserted therein. A through hole 155 is provided on the preamp housing 153 and adapted to be aligned with a through hole 157 on the arcuate disc 120 to enable an electrical conductor (not shown) to be connected to the preamp 152 and routed through the hollow shaft 136. The preamp housing 153, assembled with the preamp 152, is then inserted into the arcuate cut out 151 and held in place by the end plates 118 once the wheel 28 is assembled.

The transducer carrier assembly 30 includes the transducer carrier 38 (FIG. 10C), the transducer assembly 64 (FIG. 11) and the biasing spring 32. The transducer carrier 38 is formed in a generally rectangular shape, formed to be slightly smaller than the U-shaped cut out 138. As mentioned above, the through holes 146 in the transducer carrier 38 extend the length of the transducer carrier 38 and enable the transducer carrier 38 to be rigidly secured to the carrier disc 120. The transducer carrier 38 is also formed with a generally rectangular cut out 154, sized to conform to the square portion 40 of the transducer housing 34. The rectangular cut out 154 causes the transducer carrier 38 to be open at both ends to facilitate insertion of the transducer assembly 64 and biasing spring 32. The end plates 118 are used to close the cutout 154 in order to capture the transducer assembly 64 and biasing spring 32.

The transducer carrier assembly 30 is assembled by disposing the biasing spring 32 about the circular portion 42 of the transducer housing 34. The extending stud portion 50 of the transducer assembly 64 is then disposed in the bore 149, formed at one end of the transducer carrier 38. A through hole 156 formed on the opposite end of the transducer carrier 38 is adapted to receive the circular portion 46 of the transducer assembly 64. After the biasing spring 32 and transducer assembly 64 are assembled to the transducer carrier 38 (forming the transducer carrier assembly 30), the assembly 30 may then be secured to the transducer carrier disc 120 as discussed above.

Synchronous Drive

In accordance with another important aspect of the invention, a synchronous drive is contemplated for rotating the cylinder 26 or wheel assemblies 28, used to carry the transducers 22. These embodiments allow the rotating transducers 22 to be synchronized to the speed of the moving web 24. By synchronizing the rotation of the transducers 22 with the speed of the moving web 24, the transducer-to-web speed difference is minimized thereby minimizing undue wear to the transducer electrodes 48. Moreover, since the rotating transducers 22 are synchronized to the speed of the web 24, there is no need to partially wrap the web relative to a cylinder 26 or wheels 28 thereby avoiding an inertial load on the web 24. By eliminating the inertial load on the web 24, the system is thus adapted to be used with relatively thin paper grades, such as tissue.

Various embodiments of a synchronous drive system are contemplated. An important aspect of these embodiments is that it enables the rotating transducers 22 to be disposed on opposing sides of the moving web 24 as illustrated in FIGS. 16–21 and 23–27. As such, a configuration of the transducers 22 as illustrated in FIGS. 23–25 is contemplated which enables certain mechanical properties of the web 24 to be determined on line which do not rely on velocity measurements in the MD and the CD; for example, the polar specific stiffness. In an alternate embodiment of the invention illustrated in FIG. 28, the synchronous drive is also contemplated for a rotating cylinder disposed on one side of the moving web. By utilizing a synchronous drive, essentially no inertial load is placed on the web which enables these embodiments to be utilized with relatively thin grades of paper, such as tissue.

Referring to FIGS. 16–18, an embodiment is illustrated which utilizes three rotating wheels 160, 162 and 164. The rotating wheels 160 and 162 are disposed on one side of the moving web 24 while the rotating wheel 164 is disposed on the opposing side. The rotating wheels 160 and 162 may be mechanically synchronized to each other by way of a connecting lever 166, attached to extending drive shafts 168 and 170 of the wheels 160 and 162, respectively. If a connecting lever 166 is utilized, one or the other of the rotating wheels 160 or 162 may be driven by a servo motor 172 (FIG. 26), preferably Parker Z series servo motor, and synchronized with a servo motor 172 used to drive the wheel 164. Alternatively, the connecting lever 166 may be eliminated. In such an embodiment, each of the three wheels 160, 162 and 164 would be driven by its own servo motor 172 and synchronized together.

The use of the three rotating wheels 160, 162 and 164 enables various configurations of the transducers 22 for measuring longitudinal and shear velocity measurements. In particular, the rotating wheel 160 includes a longitudinal transducer 178 and a shear transducer 176, radially spaced therefrom as best shown in FIG. 18. Similarly, the rotating wheel 162 includes a longitudinal transducer 182 and a shear transducer 180. As shown, the longitudinal transducer 182 and the shear transducer 180 are spaced 180° apart about the wheel 162.

The wheels 160 and 162 are oriented such that the longitudinal transducers 178 and 182, carried by the wheels 160 and 162, respectively, will engage the moving web 24 at the same time. In addition, since the shear transducers 176 and 180 are spaced 180° from the longitudinal transducers 178 and 182, the shear transducers 176 and 180 will contact the moving web 24 within one half rotation of the rotating wheels 160 and 162.

The rotating wheel 164 (disposed on the opposing side of the moving web) similarly includes a longitudinal transducer 186 and shear transducer 184, spaced 180° therefrom. As best shown in FIG. 18, the system is configured such that all three of the longitudinal transducers 178, 182 and 186 contact the web 24 at the same time, while the shear transducers 176, 180 and 184 engage the web 32 within one half revolution thereof.

In an alternate embodiment of the invention as illustrated in FIGS. 19–21, a rotating cylinder 188 is utilized with two rotating wheels 190 and 192. The rotating cylinder 188 as well as the rotating wheel 190 are disposed on one side of the moving web 24, while the rotating wheel 192 is disposed on the opposing side. In order to synchronize the rotating cylinder 188 with the rotating wheel 190, a lever 194 is connected to the rotating wheel 190 by way of a crank 196 and to the rotating cylinder 188 by way of a drive shaft 198. Similar to the embodiment discussed above, the rotating cylinder 188 and rotating wheel 190 may be driven by a servo motor 172 which, in turn, is synchronized with another servo motor 172 used to drive the rotating wheel 192. Alternatively, the lever 194 may be eliminated and the cylinder 188 and wheels 190 and 192 may be driven by a servo motor 172. In such an embodiment, all three servo motors 172 are synchronized together.

The rotating cylinder 188 is provided with six transducers; three longitudinal transducers 206, 208 and 210 and three shear transducers 200, 202 and 204. The longitudinal transducers 206, 208 and 210 are spaced 180° apart from the shear transducers 200, 202 and 204 as best shown in FIG. 21.

The rotating wheel 190 is provided with a single longitudinal transducer 214 and a single shear transducer 212. The rotating wheel 190 is oriented relative to the rotating cylinder 188 such that its longitudinal transducer 214 will engage the web 24 at the same time as the longitudinal transducers 206, 208 and 210 on the rotating cylinder 188. Similarly, since the shear transducer 212 on the rotating wheel 190 is spaced apart by 180°, the shear transducer 212 on the rotating wheel 190 will also contact the moving web 24 at the same time as the shear transducers 200, 202 and 204 on the rotating cylinder 188.

The rotating wheel 192, disposed on the opposing side of the moving web 24, includes a single longitudinal transducer 218 and a single shear transducer 216, radially spaced 180° therefrom. The system is configured such that the longitudinal transducer 218 on the rotating wheel 192 engages the underside of the web 24 at the same time as the longitudinal transducers 206, 208, 210 and 214. Likewise, the system also enables the shear transducer 216 on the wheel 192 to engage the moving web 24 at the same time as the shear transducers 200, 202, 204 and 212.

In accordance with another important aspect of the present invention, the configuration of the system illustrated in FIGS. 23–25 enables non-intrusive and nondestructive determination of various mechanical properties of the web 24 which do not depend solely on velocity measurements in the MD and CD, such as the polar specific stiffness. Heretofore, measurements, such as the polar specific stiffness, have been made in a laboratory by obtaining velocity readings at every 5°–10°.

Figure 22:
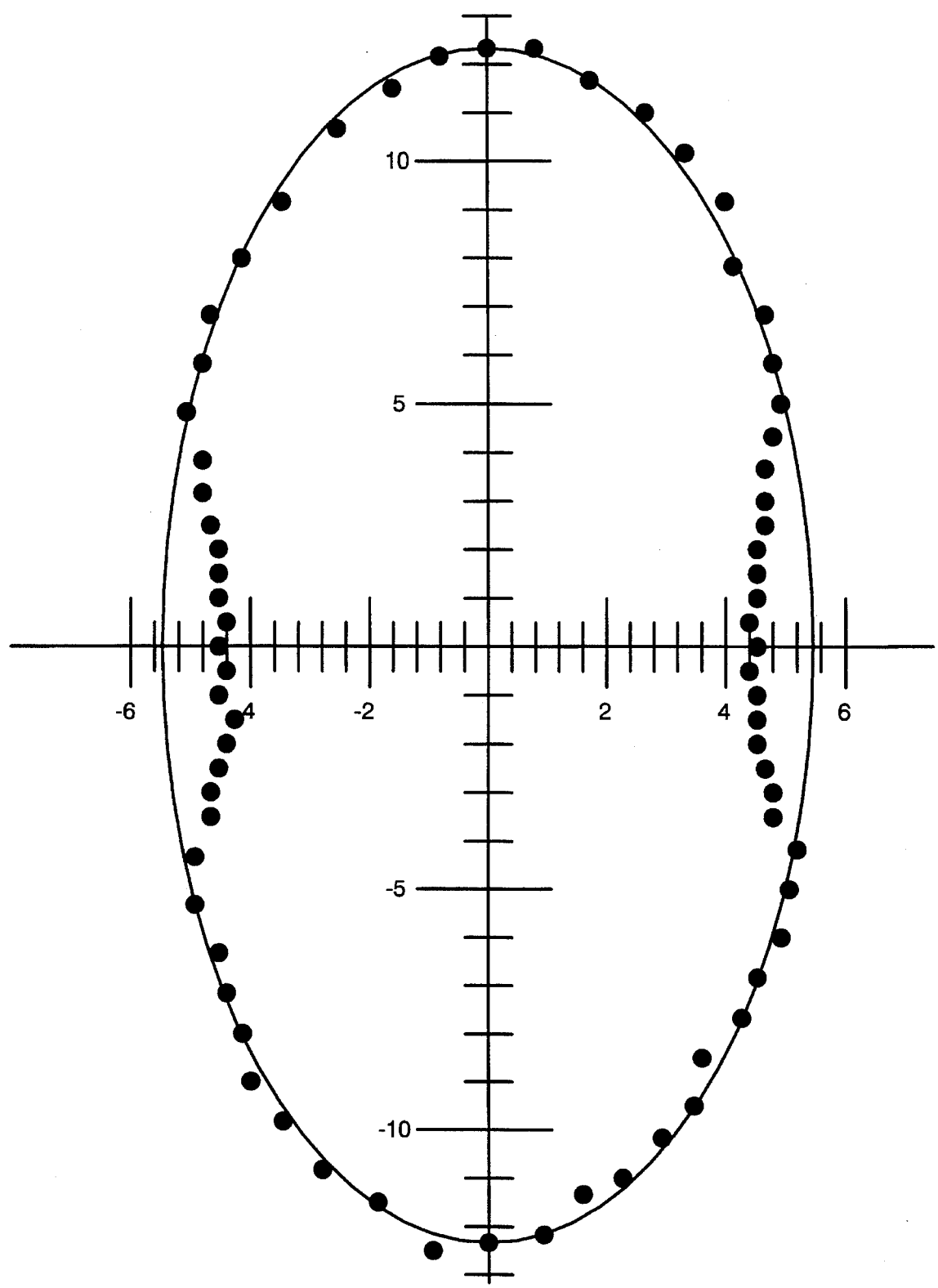
FIG. 22 is an exemplary plot of polar specific stiffness for a sample web superimposed on an ellipse.

As shown in FIG. 22, the results of such laboratory testing indicates that the polar stiffness plot is normally in the shape of a peanut. However, in accordance with the present invention, the polar stiffness plot is determined on-line by assuming that it can be approximated by an ellipse at angles away from the vicinity of the CD. Moreover, since any ellipse may be uniquely defined by three distinct points, for example, ±45° and one point at 0° (MD), such angles may be selected to determine an ellipse which provides a good approximation to the standard polar test for both polar angle and area. Since the selected points at ±45° and 0° are sufficiently removed from the CD, a satisfactory ellipse can be approximated online. However, although the points ±45° have been selected, it should be clear that other points that are sufficiently removed from the CD would also provide satisfactory results, such as ±30°.

Referring to FIGS. 23–25 a rotating cylinder 220 is disposed on one side of the moving web 24 along with a rotating wheel 222. Another rotating wheel 224 is disposed on the opposing side of the web 24. Similar to the above, the rotating cylinder 220 is mechanically synchronized to the rotating wheel 222 by way of a connecting lever 226 attached to a drive shaft 228 and a crank 230 of the rotating cylinder 220 and rotating wheel 222, respectively. One or the other of the rotating cylinder 220 or rotating wheel 222 may be driven by a servo motor 172 and synchronized with the rotating wheel 224 by way of another servo motor 172. Alternatively, the lever 226 may be eliminated. In such an application, the cylinder 220 and wheels 222 and 224 are driven by separate servo motors 172 and synchronized with each other.

The rotating cylinder 220 is provided with four transducers 230, 232, 234 and 236. The transducer 232 is oriented in the longitudinal direction, while the transducers 230 and 234 are oriented to be 45° relative to the MD. The transducer 236 is configured as a shear transducer and is disposed 180° from the transducers 230, 232 and 234.

The rotating wheel 222 includes a longitudinal transducer 240 and a shear transducer 238. The two transducers 238 and 240 are radially spaced apart by 180°. Similarly, the rotating wheel 224 includes a longitudinal transducer 244 and a shear transducer 242. The shear transducer 242 is radially spaced from the longitudinal transducer 244 by 180°.

The system is configured such that the longitudinal transducer 232 as well as the two transducers 230 and 234, oriented at 45°, engage the moving web 24 at the same time as the longitudinal transducer 240 on the rotating wheel 222 and the longitudinal transducer 244 on the rotating wheel 224. Similarly, at one half revolution thereof, the system enables the shear transducers 236, 238 and 242 to engage the moving web 24 at the same time.

In such a system, the transducer 244 on the rotating wheel 224 is configured as a transmitter and positioned such that the angle between it and each of the transducers 230 and 234 on the rotating cylinder 220 is ±45°. These two angular measurements along with the MD longitudinal measurement are sufficient to determine three points of an ellipse, thus allowing non-destructive on-line determination of the polar stiffness value.

Figure 27:
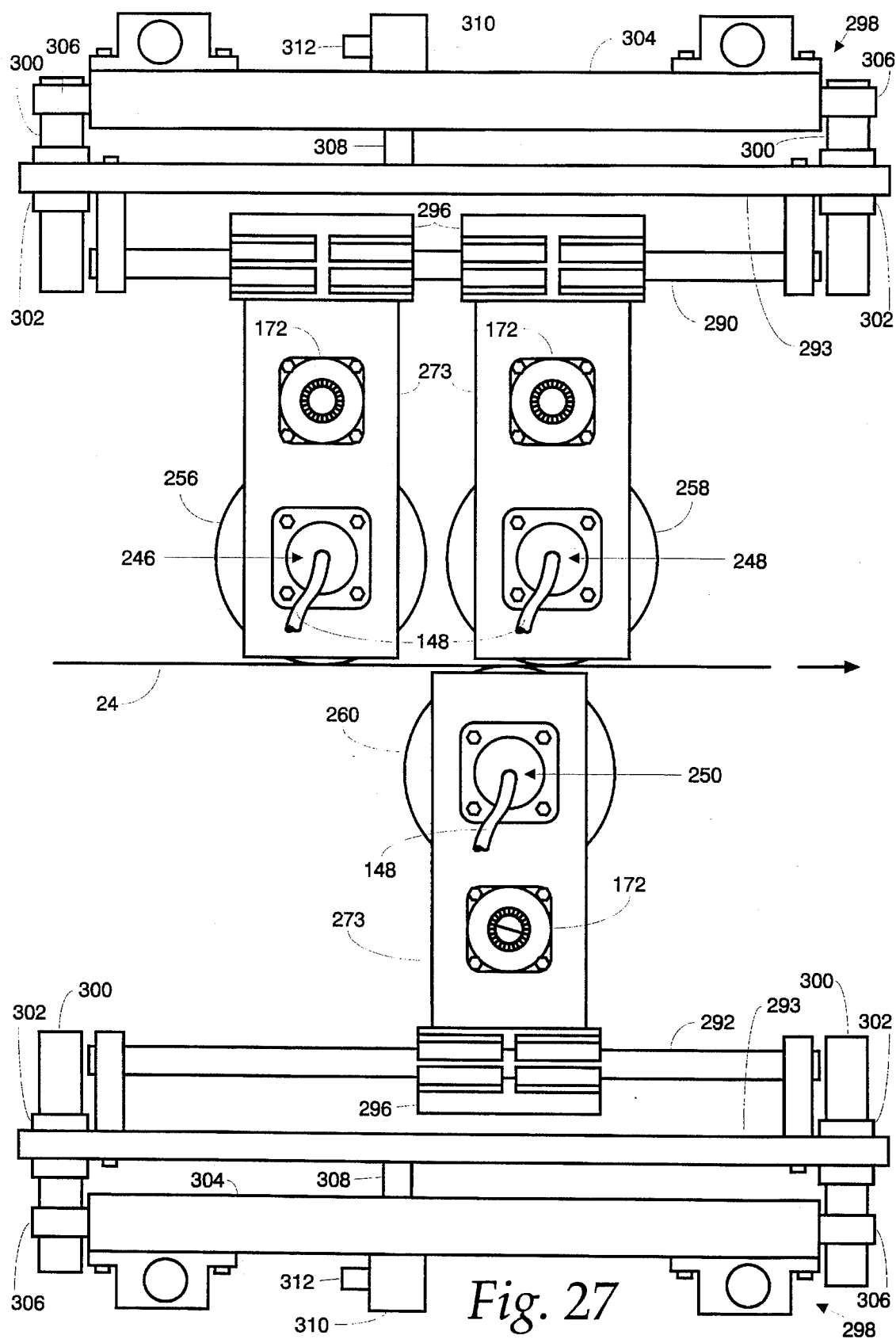
FIG. 27 is similar to FIG. 26, shown in a direction perpendicular to the direction the web is moving.
Figure 28:
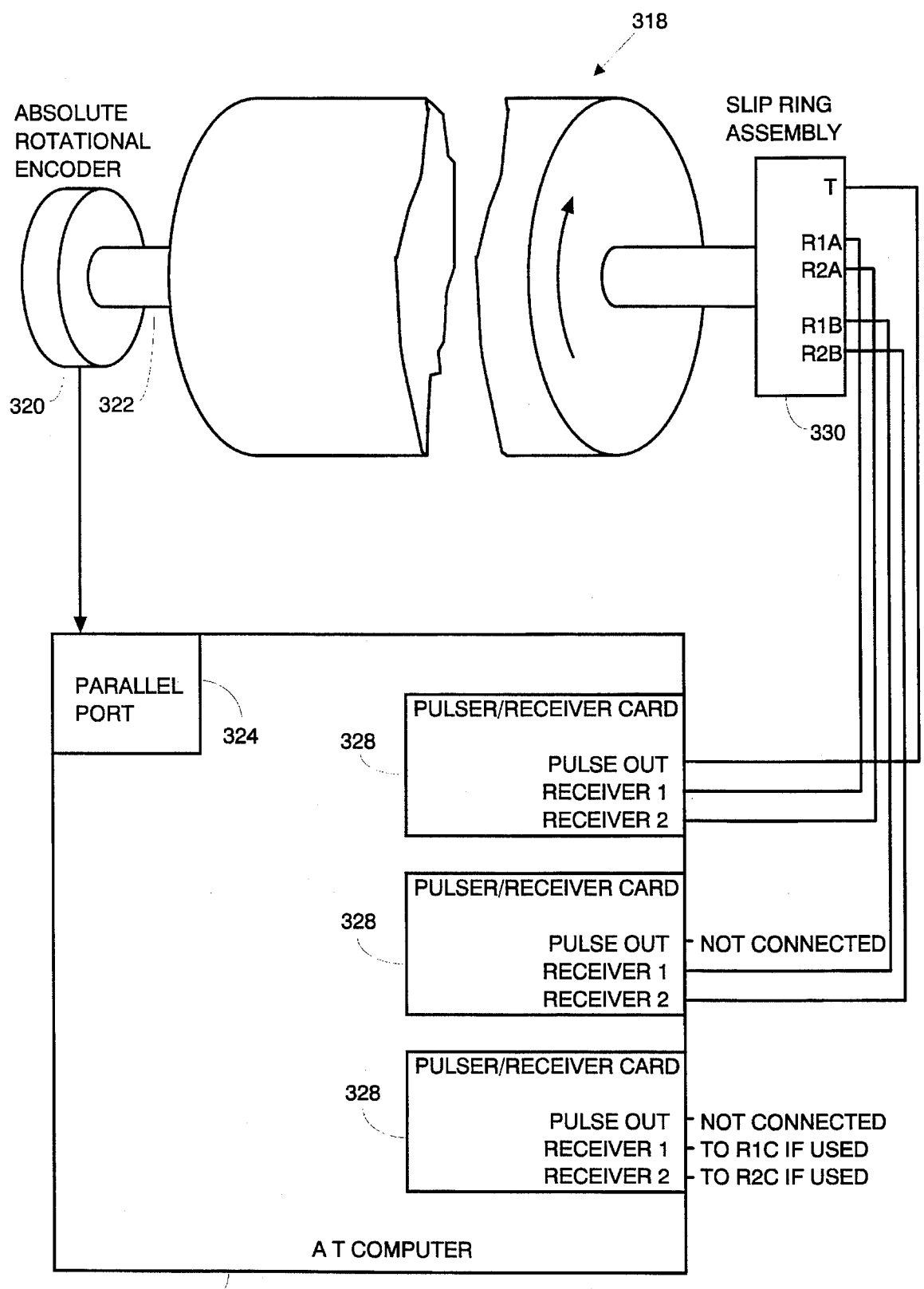
FIG. 28 is a block diagram of an alternate embodiment of a synchronous drive system in accordance with the present invention.

An exemplary physical embodiment of the synchronous drive for the system is illustrated in FIGS. 26 and 27. As shown, FIGS. 26 and 27 illustrate a system having multiple transducer wheels disposed on opposing sides of the moving web 24. FIG. 26 is a view looking in the direction of the moving web 24, while FIG. 27 illustrates a side view of the system. The system illustrated in FIGS. 26 and 27 includes a plurality of rotating wheels disposed on parallel and spaced apart axes on opposing sides of the moving web. For illustration, a system is shown with a plurality of wheels on one axis.

The system includes parallel, spaced apart axes 246 and 248 disposed on one side of the web 24 for carrying various rotating wheels to be described below. A parallel axis 250 is disposed on the opposite side of the web 24. As best shown in FIG. 26, the axis 246 carries three rotating wheels 252, 254 and 256. Since these wheels 252, 254 and 256 are all connected to the same axis 246, they will be synchronized with one another. A rotating wheel 258 (FIG. 27) is rotatably mounted with respect to the axis 248. Similarly, a rotating wheel 260 (FIG. 27) is rotatably mounted with respect to the axis 250.

Each axis 246, 248 and 250 is provided with a rotational encoder 268, disposed on one end of the axes 246, 248 and 250, to provide an indication of the rotational position of the respective wheels. Since the radial location of the various transducers 22 about the wheels 252, 254, 256, 258 and 260 is known, the encoder 268 is thus able to indicate within a predetermined range of values when the transducers disposed on the wheels 252, 254, 256, 258 and 260 are in contact with the web 24.

The synchronous drives for each of the axes 246, 248 and 250 include the servo motors 172, which include an output shaft 270. The servo motors 172 are secured to a frame 273. The output shaft 270 is coupled to a timing pulley 272 by way of a flexible coupling 274. The timing pulley 272 is rotatably carried by way of a shaft 276 which, in turn, is supported by a pair of oppositely disposed bearings 278, rigidly secured to the frame 273.

The axis 246, 248 and 250 defined by the drive shafts 136 are supported by a bearing 280 on one end, rigidly attached to the frame 273. The slip ring assembly 150 is also carried by the frame 273 and disposed adjacent the bearing 280. An electrical conductor 148 extends from the slip ring assembly 150 to provide an electrical connection between the various transducers 22 disposed in the transducer carrier assemblies 30 and an external electrical circuit, for example as illustrated in FIG. 1. The other ends of the drive shafts 136 are connected to another timing pulley 282, rotatably carried and aligned with the timing pulley 272. The timing pulley 282 is rotatably carried by a shaft 284, supported by the bearing 280. A timing belt 286, coupled between the timing pulleys 272 and 282, couples each of the drive shafts 136 with a servo motor 172 which, in turn, are synchronized with each other.

In order to provide adjustment of the frames 273 in the direction of the moving web 24, the frames 273 are slidably carried on two pairs of parallel spaced rails 290 and 292 carried by a frame 293. More particularly, the top pair of rails 290 is adapted to carry the upper frames 273 for the axes 246 and 248 while the bottom set of rails 292 is adapted to carry the bottom frame 273 for the axes 250. The frames 273 are slidably carried relative to the rails 290 and 292 by rail follower assemblies 296.

Provision may also be made to provide for vertical adjustment of the frames 273 relative to the web 24. However, in order to provide a vertical adjustment, the rails 292 for carrying the upper frames 273 may be supported by a height adjustment mechanism 298 which is automatically controlled. As such, the upper and bottom frames 273 can be spaced apart initially to enable the wheels to attain synchronous speed before engaging the moving web 24. Once the speed of the wheels is synchronized with the speed of the web, the height adjustment mechanism 298 is adjusted in order to cause the wheels to engage the web 24, thus minimizing transducer-to-web speed differences which can cause friction and undue wear of the transducers 22.

The height adjustment mechanism 298 includes a pair of vertical rails 300, rigidly coupled on one end to the frames 293 by way of coupling devices 302. The other end of the vertical rails 300 is rigidly connected to a bridge member 304 by way of a pair of coupling devices 306, rigidly secured thereto. One end of a vertical rod 308 rests on the frame 293. The other end of the rod 308 is secured to an air cylinder 310 with an extending pneumatic fitting 312. The cylinder 310 allows the vertical rod 308 to be moved upwardly and downwardly to vary the distance between the upper and lower frames 293.

In an alternate embodiment of the system, a synchronously-driven cylinder 318 (FIG. 28) is contemplated. The cylinder 318 is similar to the cylinder 26 discussed above with the exception that it includes an absolute rotational encoder 320, rigidly connected to a shaft 322, extending outwardly from the cylinder 318. As mentioned above, the absolute rotational encoder 320 is used to provide an indication of the rotational position of the cylinder 318. The rotational position information from the absolute encoder 320 is applied to a parallel port 324 in a computer 326, for example a type IBM PC/AT or compatible personal computer.

The rotational position information is utilized to enable the computer 324 to control a plurality of pulser/receiver control cards 328 within the computer 324. The pulser/receiver control cards 328 are electrically connected to a slip ring assembly 330, attached to the shaft 322, to provide and receive electrical power relative to the transducers 22 carried by the cylinder 318. During a valid range of rotation, the computer 324 causes the pulser/receiver cards 328 to pulse and begin digitizing received signals.

Friction Drive Embodiment

Figure 29:
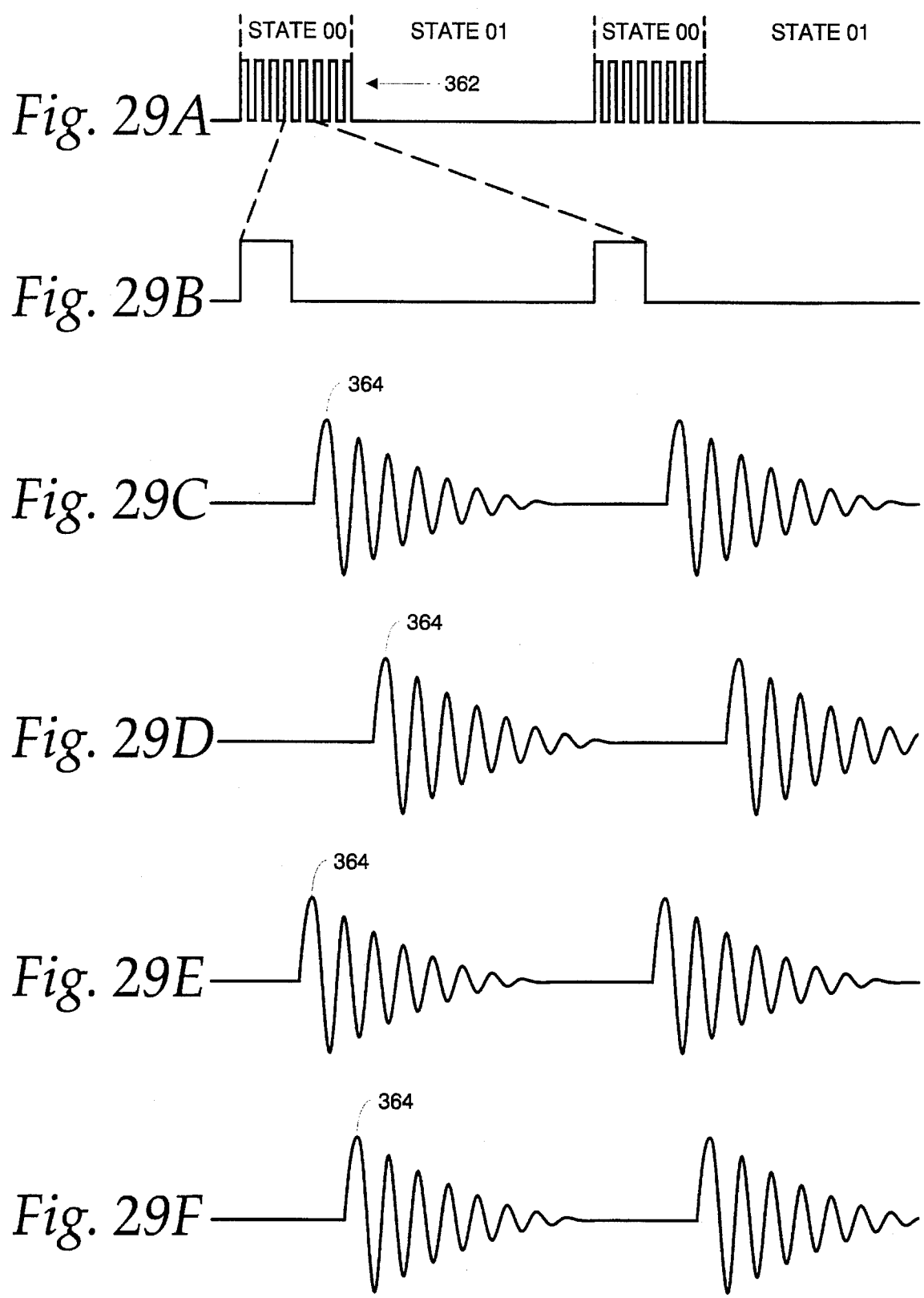
FIGS. 29A–29F are timing diagrams for the ultrasonic testing system illustrated in FIG. 1.
Figure 30:
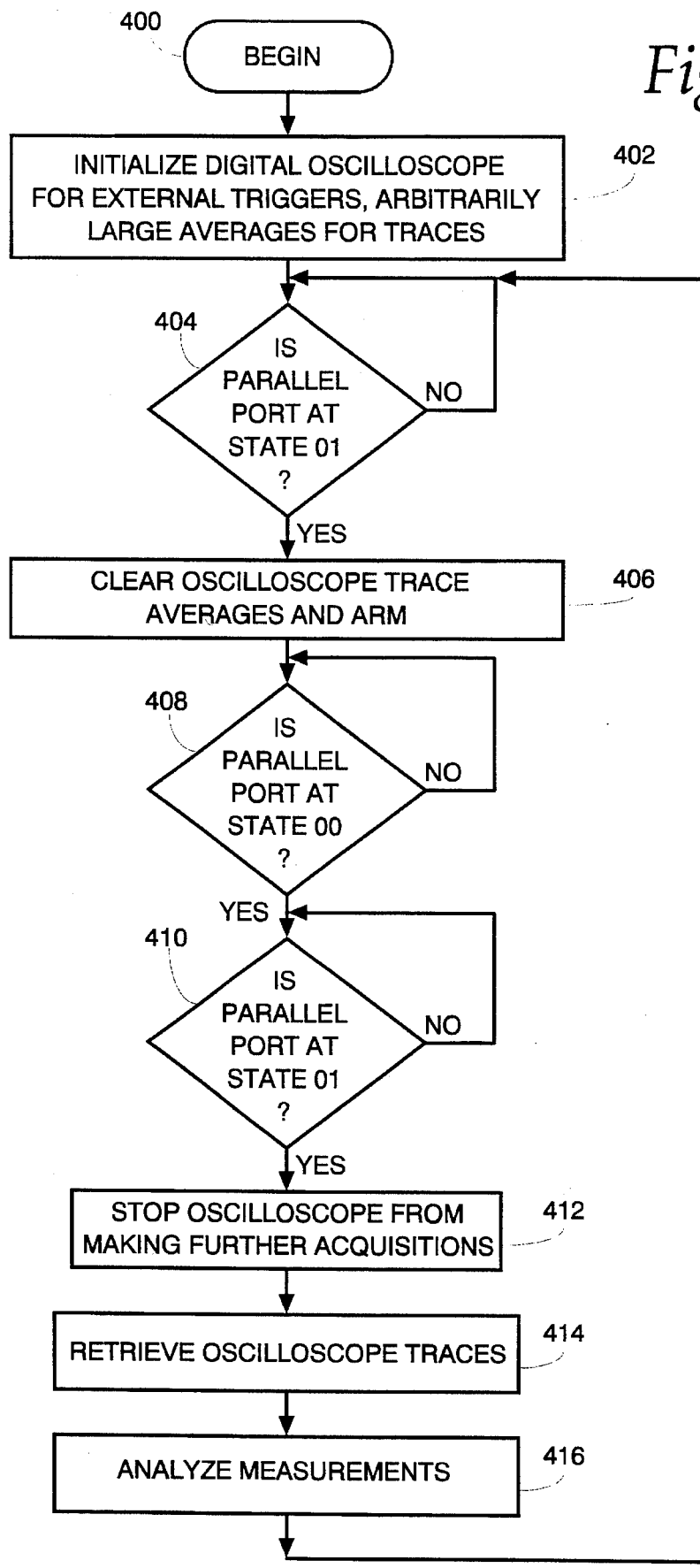
FIG. 30 is a flow chart for the ultrasonic testing system illustrated in FIG. 1.

In addition to the synchronously-driven embodiments discussed above, an improvement of a friction-driven system is illustrated in FIGS. 1, 29 and 30. In this embodiment, the transducers 22 (FIG. 1) are carried by the cylinder 26 in the manner described above in order to provide relatively constant contact force between the transducers 22 and the web 24.

One transducer 22 serves as a transmitter (T), positioned to excite longitudinal waves in the web 24 in the direction of the web and shear waves in the CD direction. The other four transducers are positioned relative to the transmitter (T) into two sets of receivers (R1A, R2A and R1B, R2B). The receiver sets (R1A, R2A and R1B, R2B) are positioned at different distances in order to create a path length difference from the transmitter to the receivers.

The receiver set R1A, R2A is aligned with the transmitter T in the CD direction and is oriented to detect CD shear waves. The other receiver set (R1B, R2B) is positioned in the MD direction and is used to excite longitudinal waves in the MD direction.

In such a system, the web 24 is partially wrapped about the cylinder 26 in order to provide a friction drive. During an active measurement region, the transmitter T is excited by a continuous stream of single cycle ultrasonic pulses, spaced at approximately 1 millisecond interval. This pulse interval is selected to enable ultrasonic pulses in the web 24 from the last excitation to die out. Each excitation causes the transmitter T to launch ultrasonic signals in the plane of the web in all directions. These signals are received by the receiver sets R1A, R2A and R1B, R2B and captured by a digitizing oscilloscope 340. In particular, the ultrasonic signals from the receivers R1A, R2A and R1B and R2B are fed into channels 1–4 of the digitizing oscilloscope 340. These signals are averaged by the digitizing oscilloscope 340 during the active region as illustrated in FIGS. 29C–F. After the signals are averaged, the oscilloscope 340 takes time measurements of the corresponding half cycle peaks. The time of the most positive peak of each of the four oscilloscope traces is then determined. More particularly, the peak times of the longitudinally-propagating waves W1B and W2B (FIG. 1) are subtracted to obtain a pulse flight time between the receivers R1B and R2B. The same is done for the receivers R1A and R2A. Knowing the distances and travel times between the receiver pairs enables the velocities to be calculated.

The system for implementing the method for calculating the in-plane velocities is illustrated in FIG. 1. In addition to the rotating cylinder 26 and the transducers 22, the system includes a proximity sensor system 350 for indicating when the transducers 22 are in contact with the web 24 (e.g., the active region). A slip ring assembly 352, attached to a drive shaft 354, provides an electrical connection between the transducers 22 on the cylinder 26 and the balance of the circuitry. In particular, the slip ring assembly, preferably a Michigan Scientific Series S6, provides connections between the receiver sets R1A, R2A and R1B, R2B and channels 1–4 of the digitizing oscilloscope 340 by way of ultrasonic preamplifiers 152, preferably Parametrics Series 566OB. The slip ring assembly 352 also enables a electrical signal from a function generator 358, preferably a WaveTek Model 143 20 mHz function generator, to be connected to the transmitter T.

The system is under the control of a two-state state machine 360. As best shown in FIGS. 29A and 29B, the state machine 360 generates an active state, state 00, during which the transmitter 22 is excited and pulse flight times are measured and an inactive state, state 01. During active states, a series of excitation pulses 362 (FIG. 29A) are generated. In response to each excitation pulse 362, shown exaggerated in FIG. 29B, the pulse flight times between the receiver sets R1A, R2A and R1B, R2B are measured. The pulse flight times of these signals are averaged during the active state (e.g., state 00), as illustrated in FIGS. 29C–29F. In particular, the time difference between the most positive peaks 364 between signals W1A, W2A and W1B, W2B is determined in order to calculate the velocity of the ultrasonic signals in the longitudinal and shear directions as discussed above.

The proximity sensor system 350 drives the state machine 360. In particular, the system 350 includes a pair of metal targets 366 and 368, disposed on a collar 370 on the output shaft 354 of the cylinder 26. These targets 366 and 368 are used to indicate the non-active and active periods. In particular, the target 366 is positioned to sense the condition when the transducers 22 have just left contact with the web 24. This target 366 is sensed by a sensor 371, for example a Hall effect sensor, and applied to the CLOCK input of a four-state roll-around counter 372, which may be a ring counter, to control the state machine 360. The other target 368 is mounted to indicate when all of the transducers 22 have just come into contact with the web 24. This target 368 is sensed by a sensor 374 and applied to the CLEAR input of the state machine roll-around counter 372.

As mentioned above, a series of excitation pulses 362 (FIGS. 29A and 29B) are applied to the system during an active state (e.g., state 00). More particularly, a 5 v, 1 kHz squarewave generator 378, preferably a Dynascan Corp. Model 3020 Sweep/Function generator, is connected to an input of the three-channel analog multiplexer 380. During active states, the squarewave generator 378 is connected to an output B2 which, in turn, is connected to an external trigger of the function generator 358 which, in turn, triggers the digitizing oscilloscope 340 and sends the excitation pulse 362 to the transmitter T by way of a slip ring assembly 352. During non-active states (e.g., state 01), the squarewave generator 378 is connected to the multiplexer outputs B1 and B3, which are unconnected.

In order to provide an indication of the state of the machine 360, a 5-volt input 382 is applied to outputs A1, A2 and A3 of the analog multiplexer 380. The A1, A2, A3 outputs are connected to a parallel port 384 in a digital computer 386, for example, a personal computer based on an Intel 80386 microprocessor or better. Since the output A1, A2 and A3 are controlled by a roll-around counter 372, the +5-volt from the +5-volt supply 382 will be applied to the parallel port to indicate the state of the state machine 360.

The signal data from the digitizing oscilloscope 340, preferably a LeCroy Model 7200, is applied to the digital computer 386 by way of a general purpose interface bus 388 (GPIB), preferably a Model No. GPIB-CIIA from National Instruments Company. The GPIB 388 is interconnected between GPIB interface 390 and 392 on the digital computer 386 and digitizing oscilloscope 340, respectively.

A flow diagram for the digital computer 386 is illustrated in FIG. 30. The system begins at step 400. Initially, the system initializes the digital oscilloscope 340 for external triggers and arbitrarily large averages for traces in step 402. Next, the system determines if the parallel port 384 is at state 01 in step 404. If not, the system cycles back to step 404. Once the parallel port is determined to be at state 01, the oscilloscope trace averages are cleared in step 406. The oscilloscope 340 is also armed in this step 406. Subsequently, the system monitors the parallel port 384 in step 408 to determine if the system is at state 00. If not, the system cycles back to step 408. Once the system is at state 00, the digital oscilloscope 340 capture ultrasonic signals until the system reaches state 01, as determined in step 410. Subsequently, after the system reaches state 01, the system proceeds to step 412 where the oscilloscope 340 is disabled from making further data acquisitions. Subsequently in step 414, the traces are retrieved and the information is analyzed by the digital computer 386 in state 416. The system then recycles back to step 404 for the next active state.

Obviously, many modifications and variations of the present invention are possible in light of the above teachings. Thus, it is to be understood that, within the scope of the appended claims, the invention may be practiced otherwise than as specifically described above.

What is claimed and desired to be secured by Letters Patent of the United States is:

1. A cylinder assembly for carrying one or more ultrasonic transducers, said transducers adapted to be in rolling contact with a moving web of a predetermined material, the cylinder assembly comprising:

one or more predetermined ultrasonic transducers; one or more transducer housings for rigidly carrying each of said one or more ultrasonic transducers to form one or more transducer housing assemblies, at least a portion of each of said transducer housings being formed with a generally square cross-section to facilitate radial orientation of said one or more transducer housing assemblies relative to a transducer carrier;

a transducer carrier for carrying said transducer housing assemblies, said transducer carrier being formed with a bore with a generally square cross-section to correspond with said generally square cross-sectional portion of said transducer housing assembly to facilitate radial orientation of said transducer housing assembly relative to said transducer carrier, while enabling said transducer housinq assembly to be carried by said transducer carrier in one of a plurality of radial orientations; and a cylinder formed with a plurality of radial cutouts for rigidly carrying said transducer carriers.

2. A cylinder assembly as recited in claim 1, further including means for capturing said transducer housing assemblies relative to said transducer carrier.

3. A cylinder assembly as recited in claim 2, wherein said capturing means includes end plates adapted to be rigidly secured to said transducer carrier to close said central bore.

4. A cylinder assembly as recited in claim 1, further including means for biasing said transducer assembly relatively outwardly relative to said transducer carrier.

5. A wheel assembly for carrying ultrasonic transducers, comprising: a transducer carrier disc formed with a central bore and one or more generally rectangular cutouts, radially oriented about said disc;

one or more transducer carriers for carrying one or more ultrasonic transducers, each of said transducers adapted to be rigidly secured in said generally rectangular cutouts in said transducer carrier disc; and means for capturing said transducer carrier relative to said transducer carrier disc.

6. A wheel assembly for carrying ultrasonic transducers, comprising:

a transducer carrier disc formed with a central bore and one or more radial cutouts;

a transducer carrier for slidably carrying an ultrasonic transducer adapted to be rigidly secured in said radial cutout, wherein said transducer carrier is formed in a generally rectangular shape, sized to be slightly smaller than said cutout, formed to be generally rectangular in shape for receiving an ultrasonic transducer.

7. A wheel assembly as recited in claim 6, further including means for biasing said ultrasonic transducer radially outwardly relative to said transducer carrier.

* * * * *